United States Patent
Escribá Ruiz et al.

(10) Patent No.: US 10,588,883 B2
(45) Date of Patent: Mar. 17, 2020

(54) ALPHA-DERIVATIVES OF CIS-MONOUNSATURATED FATTY ACIDS FOR USE AS MEDICINES

(71) Applicant: UNIVERSITAT DE LES ILLES BALEARS, Palma de Mallorca (ES)

(72) Inventors: Pablo Vicente Escribá Ruiz, Palma de Mallorca (ES); Xavier Busquets Xaubet, Palma de Mallorca (ES); Gwendolyn Barceló Coblijn, Palma de Mallorca (ES); Victoria Lladó Cañellas, Palma de Mallorca (ES); Rafael Álvarez Martínez, Palma de Mallorca (ES); Silvia Teres Jiménez, Palma de Mallorca (ES); Daniel López, Palma de Mallorca (ES); Juana Barceló Estarellas, Palma de Mallorca (ES); Julian Taylor Green, Toledo (ES); Gerardo Ávila Martín, Toledo (ES)

(73) Assignee: UNIVERSITAT DE LES ILLES BALEARS, Palma de Mallorca (ES)

( * ) Notice: Subject to any disclaimer, the term of this patent is extended or adjusted under 35 U.S.C. 154(b) by 0 days.

(21) Appl. No.: 15/645,524

(22) Filed: Jul. 10, 2017

(65) Prior Publication Data
US 2018/0193297 A1 Jul. 12, 2018

Related U.S. Application Data

(63) Continuation of application No. 14/664,351, filed on Mar. 20, 2015, now Pat. No. 9,730,906, which is a continuation of application No. 13/132,231, filed as application No. PCT/ES2009/070561 on Dec. 4, 2009, now Pat. No. 9,000,042.

(30) Foreign Application Priority Data

Dec. 9, 2008 (ES) .................................. 200803480

(51) Int. Cl.
*A61K 31/185* (2006.01)
*A61K 31/201* (2006.01)
*A61K 31/231* (2006.01)
*A23L 33/12* (2016.01)

(52) U.S. Cl.
CPC ............ *A61K 31/201* (2013.01); *A23L 33/12* (2016.08); *A61K 31/185* (2013.01); *A61K 31/231* (2013.01)

(58) Field of Classification Search
CPC ... A61K 31/201; A61K 31/185; A61K 31/231
See application file for complete search history.

(56) References Cited

U.S. PATENT DOCUMENTS

| | | | |
|---|---|---|---|
| 3,872,141 A | 3/1975 | Weis et al. | |
| 3,931,306 A | 1/1976 | Hall et al. | |
| 4,241,097 A | 12/1980 | Hall et al. | |
| 4,551,279 A | 11/1985 | Mueller et al. | |
| 4,808,403 A | 2/1989 | Wilson et al. | |
| 5,198,250 A | 3/1993 | Brillhart et al. | |
| 5,208,260 A | 5/1993 | Cordi | |
| 5,504,107 A | 4/1996 | Mantri et al. | |
| 5,856,537 A | 1/1999 | Lerner et al. | |
| 6,274,624 B1 | 8/2001 | Nau et al. | |
| 6,702,756 B2 * | 3/2004 | Brown | A61B 5/00 600/300 |
| 7,462,349 B2 | 12/2008 | Kalderon | |
| 7,851,507 B2 | 12/2010 | Escriba-Ruiz | |
| 8,193,245 B2 | 6/2012 | Kim et al. | |
| 8,324,167 B2 | 12/2012 | Bar-or et al. | |
| 9,000,042 B2 | 4/2015 | Escriba Ruiz | |
| 2004/0053789 A1 | 3/2004 | Jones et al. | |
| 2004/0214215 A1 | 10/2004 | Yu et al. | |
| 2005/0014831 A1 | 1/2005 | Escriba-Ruiz | |
| 2005/0090399 A1 | 4/2005 | Friedmann et al. | |
| 2012/0252967 A1 | 10/2012 | Ercole et al. | |

FOREIGN PATENT DOCUMENTS

| | | |
|---|---|---|
| CN | 1688302 A | 10/2005 |
| FR | 2609032 A1 | 7/1988 |
| JP | S4928172 B1 | 7/1974 |
| JP | S60208951 A | 10/1985 |
| JP | H05139947 A1 | 6/1993 |
| JP | H09110635 A | 4/1997 |
| JP | H10505064 A | 5/1998 |

(Continued)

OTHER PUBLICATIONS

Alemany, R. et al.; "2-Hydroxyoleic Acid A New Hypotensive Molecule," Hypertension, 2004, pp. 249-254, vol. 13, available online Dec. 8, 2003.
Escriba, P.V.; "Membrane-lipid therapy: a new approach in molecular medicine," Trends in Molecular Medicine. 2006, pp. 34-43, vol. 12, available online Dec. 1, 2005.
Magrioti, V., et al.; "Synthesis of (S)—α—Amino Oleic Acid," Lipids, 2002, pp. 223-228, vol. 37.
Chemical Abstracts Service Registry No. 155056-28-3, 9-octadecenoic acid, 2-fluoro-, (9Z)-, Date of entry into the STN Database: May 13, 1994.
Chemical Abstracts Service Registry No. 339170-34-2, 9-octadecenoic acid, 2-hydroxy-, methyl ester, (2S, 9Z)-, Date of entry into STN Database: Jun. 1, 2001.

(Continued)

*Primary Examiner* — Jennifer M Kim
(74) *Attorney, Agent, or Firm* — Tristan A. Fuierer; Olive Law Group, PLLC

(57) ABSTRACT

Alpha-derivatives of cis-monounsaturated fatty acids for use as medicines. The present invention refers to pharmaceutically acceptable compounds of Formula I, their salts and derivatives, where (a) and (b) can take any value between 0 and 14, (X) can be substituted by any atom or group of atoms with an atomic/molecular weight between 4 and 200 Da and (R) can be substituted by any atom or group of atoms with an atomic/molecular weight between 1 and 200 Da, for use as medicines.

15 Claims, 19 Drawing Sheets

(56) References Cited

FOREIGN PATENT DOCUMENTS

| JP | H110504523 A | 5/1998 |
|---|---|---|
| JP | H10182338 A | 7/1998 |
| JP | 2001523695 A | 11/2001 |
| SU | 1098539 A | 6/1984 |
| WO | 9201450 A1 | 2/1992 |
| WO | 0135939 A2 | 5/2001 |
| WO | 2003030891 A1 | 4/2003 |
| WO | 2003062244 A1 | 7/2003 |
| WO | 2004080468 A1 | 9/2004 |
| WO | 2005041691 A1 | 5/2005 |
| WO | 2007021061 A1 | 2/2007 |
| WO | 2007069758 A1 | 6/2007 |
| WO | 2009127009 A1 | 10/2009 |
| WO | 2009127012 A1 | 10/2009 |

OTHER PUBLICATIONS

Chemical Abstracts Service Registry No. 339170-33-1, 9-octadecenoic acid, 2-hydroxy-, methyl ester, (2R, 9Z-, Date of entry into STN Database: Jun. 1, 2001.

Chemical Abstracts Service Registry No. 56472-30-1, 9-octadecenoic acid, 2-hydroxy-, methyl ester, (9Z)-, Date of entry into STN Database: Nov. 16, 1984.

Chemical Abstracts Service Registry No. 760938-73-6, 9-octadecenoic acid, 2-amino-, methyl ester, (2S, 9Z)-, Date of entry into STN Database: Oct. 12, 2004.

Chemical Abstracts Service Registry No. 434938-02-0, 9-octadecenoic acid, 2-amino-, methyl ester, hydrochloride (1:1), (2S, 9Z)-, Date of entry into STN Database: Jun. 28, 2002.

Martinez, et al., "Membrane structure modulation, protein kinase Calpha activation, and anticancer activity of Mineral," Molecular Pharmacology, 2005, pp. 531-540, vol. 67.

Adonizio et al., "Temozolomide in non-small cell lung cancer: preliminary results of a phase II trial in previously treated patients," Clinical Lung Cancer, 2002, pp. 254-258, vol. 3.

Zanger, et al.; "Structure-Activity Relationship and Drug Design," Remington's Pharmaceutical Sciences (Sixteenth Editon). Mack Publishing. 1980, pp. 420-425.

Llado, V. et al.; "Minerval induces apoptosis in Jurkat and other cancer cells," Journal of Cellular and Molecular Medicine, 2008, vol. 14, pp. 659-670.

Llado, V., et al.; "Molecular basis of the antiproliferative effect of 2-hydroxy-9-cis-octadecenoid acid (Minerval) in human leukemia Jurkat cells," Chemistry and Physics of Lipids, 2007, vol. 149, 48th International Conference on the Bioscience of Lipids; Turku, Finland; (Sep. 4-8, 2007).

Chen, W., et al.; "Synergistic inhibition of calcification of porcine aortic root with preincubation in FeCl3 and alpha-amino oleic acid in a rat subdermal model," Journal of Biomedical Materials Research, 1997, vol. 38 (1), pp. 43-48.

Markidis, T., et al.; "Synthesis and in vitro cytotoxicity of long chain 2-amino alcohols and 1,2-diamines," Anticancer Research, 2001, vol. 21, pp. 2835-2839.

Martinez, J., et al.; "The repression of E2F-1 is critical for the activity of minerval against cancer," Journal of Pharmacology and Experimental Therapeutics, 2005, vol. 313, pp. 466-474.

Jesnke, R., et al.; "Gas chromatography/electron-capture negative ion mass spectrometry for the quantitative determination of 2- and 3-hydroxy fatty acids in bovine milk fat," Journal of Agricultural and Food Chemistry, 2008, vol. 56, pp. 5500-5505.

Hwang, H.-S., et al., "Highly selective asymmetric synthesis of 2-hydroxy fatty acid methyl esters through chiral oxazolidinone carboximides," Journal of the American Oil Chemists Society, 2001, vol. 78, pp. 205-211.

Oliver, J. E., et al., "A convenient synthesis of alpha-fluoro carboxylic acids," Synthesis, 1994, vol. 3, pp. 273-275.

Yokozawa, T., et al.; "Alpha-Acylation and -allylation of β,β,β-trifluoropropionic esters via the ketene silyl acetals," Tetrahedron Letters, 1984, vol. 25, pp. 3991-3994.

Carballeira, N. M., et al.; "Facile total synthesis and antimicrobial activity of the marine fatty acids (Z)-2-methoxy-5-hexadecenoic acid and (Z)-2-methoxy-6-hexadecenoic acid," Journal of Natural Products, 1998, vol. 61, pp. 1543-1546.

Adam, W., et al.; "Synthesis of optically active α-hydroxy acids by kinetic resolution through lipase-catalyzed enantioselective acetylation," European Journal of Organic Chemistry, 1998, vol. 9, pp. 2013-2018.

Tanaka, K., et al.; "(Allylthio)acetate dianion as a new and convenient reagent for the stereoselective synthesis of (2E,4E)dienoates from alkyl halides," Chemistry Letters, 1981, vol. 3, pp. 315-318.

Padron, J. M., et al., "Enantiospecific synthesis of α-amino acid semialdehydes: a key step for the synthesis of unnatural unsaturated and saturated α-amino acids," Tetrahedron: Asymmetry, 1998, vol. 9, pp. 3381-3394.

Carballeira, N. M., et al.; "New methoxylated fatty acids from the Caribbean sponge Callyspongia fallax," Journal of Natural Products, 2001, vol. 64, pp. 620-623.

Carballeira, N. M., et al.; "Novel methoxylated FA from the Caribbean sponge *Spheciospongia cuspidifera*," Lipids, 2002, vol. 37, pp. 305-308.

Klun, J. A., et al.; "Evidence of pheromone catabolism via β-oxidation in the European corn borer (*Lepidoptera*: Crambidae)," Journal of Entomological Science, 1998, vol. 33, pp. 400-406.

Ayanoglu, E., et al.; "Phospholipid studies of marine organisms: V. New α-methoxy acids from Higginsia tethyoids," Lipids, 1983, vol. 18, pp. 830-836.

Mikami, K., et al., "Novel silyl triflate-mediated [2, 3]Wittig sigmatropic rearrangement. The possible intervention of an oxygen ylide," Tetrahedron Letters, 1986, vol. 27, pp. 4511-4514.

Duthaler, R. O.; "Synthesis of β,γ-unsaturated D-α-amino acids from L-cysteine," Angewandte Chemie International Edition, 1991, vol. 30, pp. 705-707.

Schoellkopf, U., et al.; "Asymmetric synthesis via heterocyclic intermediates: VII. Enantioselective synthesis of (R)-α-amino acids using (S)-0,0-dimethyl-α-methyldopa as a chiral auxiliary reagent," Synthesis, 1981, vol. 12, pp. 966-969.

Carballeira, N. M., et al.; "New 2-Hydroxy Fatty Acids in the Caribbean Urchin *Tripneustes esculentus*," Journal of Natural Products, 1994, vol. 57, pp. 614-619.

Drigues, P., et al.; "Study of the Phospholipids of Pseudomonas Solanacearum Occurrence of Monoenoic α-Hydroxylated Fatty Acids," Biochimica et Biophysica Acta, 1981, vol. 666, pp. 504-507.

\* cited by examiner

Figure 4A
Figure 4B
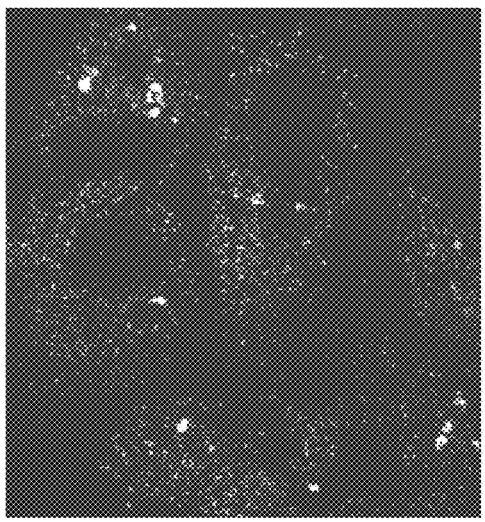
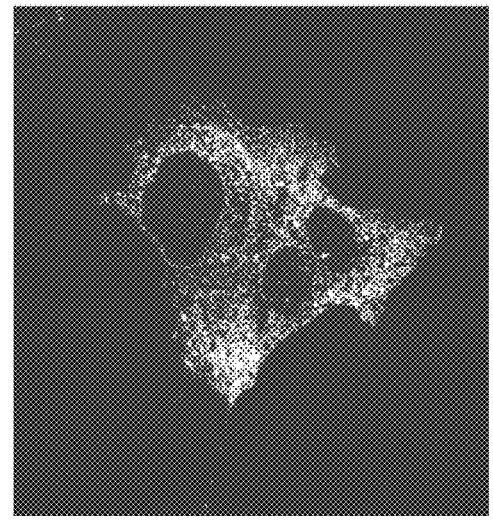
Figure 5A
Figure 5B
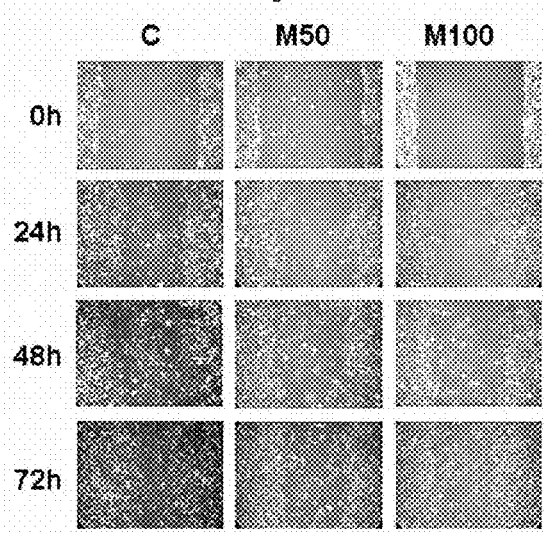
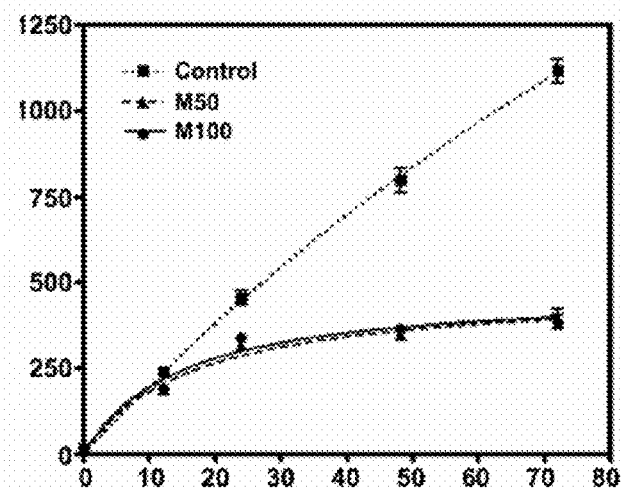

ALPHA-DERIVATIVES OF CIS-MONOUNSATURATED FATTY ACIDS FOR USE AS MEDICINES

CROSS-REFERENCE TO RELATED APPLICATIONS

This application is filed under the provisions of 35 U.S.C. § 111(a) and is a continuation of U.S. patent application Ser. No. 14/664,351 filed on Mar. 20, 2015, and entitled "ALPHA-DERIVATIVES OF CIS-MONOUNSATURATED FATTY ACIDS FOR USE AS MEDICINES" in the name of Pablo Vicente ESCRIBÁ RUIZ, et al., which claims priority to U.S. patent application Ser. No. 13/132,231 filed 22 Aug. 2011, now U.S. Pat. No. 9,000,042 issued on Apr. 7, 2015, which claims the priority of International Patent Application No. PCT/ES2009/070561 filed on 4 Dec. 2009, which claims priority of Spanish Patent Application No. P200803480 filed on 9 Dec. 2008, all of which are hereby incorporated by reference herein in their entirety.

FIELD OF THE INVENTION

The present invention refers to pharmaceutically acceptable α-derivatives of cis-monounsaturated fatty acids of Formula I, their salts or derivatives (see the description of the invention), to be used as medicines, preferably in the prevention and/or treatment of diseases where the underlying aetiology is based on changes (from any cause) in the lipids of the cellular membrane such as, for example, changes in the level, composition or structure of these lipids. It also refers to their use for pathologies in which regulation of the lipid composition and structure of the membrane causes a reverse of the pathological state. In addition, in the present invention, the use of compounds of Formula I, where (X) is replaced by OH, $NH_2$ or $CH_3$ and (R) is replaced by H, for the prevention and treatment of cardiovascular diseases and obesity and for the treatment of lung, brain or prostate cancer in humans is excluded.

Thus, the present invention, due to its wide application spectrum, can be included in the general field of medicine and pharmacy.

STATE OF THE ART

Cellular membranes are structures that define the entity of cells and of the organelles that they contain. The majority of biological processes occur in or close to membranes and their constituent lipids not only have a structural role but also regulate the activity of important processes. Furthermore, the regulation of the lipid composition of the membranes also influences the location or function of important proteins involved in the control of cellular physiology such as protein-G and PKC (Escribá et al., 1995; 1997; Yang et al; 2005; Martínez et al., 2005). These and other studies demonstrate the importance of lipids in the control of important cellular functions. In fact, many human diseases including: cancer, cardiovascular pathologies, neurodegenerative processes, obesity, metabolic disorders, inflammation, infectious diseases and autoimmune diseases have been related to changes in the levels or in the composition of the lipids present in biological membranes. Further evidence is provided by the beneficial effects of treatments with fatty acids other than those of the present invention that regulate the composition and structure of membrane lipids, where they are employed to reverse such diseases (Escribá, 2006).

Lipids that are ingested in the diet regulate the lipid composition of cellular membranes (Alemany et al., 2007). Also, various physiological and pathological situations can change the lipids present in cellular membranes (Buda et al., 1994; Escribá, 2006). Changes in the lipid composition of membranes affects cellular signalling, potentially giving rise to disease development or in reversing disease progression (Escribá, 2006). Saturated fatty acids ingested in food have some negative effects on the composition and structure of the membrane that can give rise to various pathologies such as cancer, metabolopathies (diabetes, hypercholesterolemia, hypertriglyceridemia, etc.), obesity, heart and vascular diseases, inflammation, neurodegenerative processes, etc. This theory would also explain the changes caused by other fats such as denatured colza oil, which at one time caused a toxic syndrome with devastating consequences leading to permanent invalidity and death in many cases. By contrast, those lipids with beneficial health effects, are beneficial for all cells and, therefore, can act on multiple pathological processes, which implies that the fatty acids of the present invention have a broad therapeutic spectrum.

Additionally, therapies involving regulation of the structure and/or function of membrane lipids can be applied to pathologies in which these lipids do not show significant changes, but as a result of interventions made on them (through pharmaceutical or nutraceutical means) cellular function is modulated, reversing the pathological process.

Various studies performed in recent years have indicated that membrane lipids have a very much more important role than has been appreciated to date (Escribá et al., 2008). An example of this importance is shown in fish living in rivers where the temperature varies, whose lipids undergo significant changes (in membrane composition and in lipid types) when the temperature falls from 20° C. (summer) to 4° C. (winter) (Buda et al. 1994). Such studies demonstrate that changes in membrane lipids give rise to a series of coordinated changes in cellular functions to maintain correct cellular physiology. In the case of fish living in water of variable temperature, regulation of membrane lipids allows maintenance of functions in very diverse cell types. Therefore it can be said that membrane lipids can determine good or poor functioning of multiple cell signalling mechanisms.

Given that a diseased organism is diseased because its cells are diseased, changes in membrane lipids can give rise to the appearance of diseases. Analogously, therapeutic, nutraceutic or topical/cosmetic interventions directed at regulating membrane lipid levels can prevent or reverse (cure) pathological processes. Additionally, many studies have indicated that the consumption of saturated and trans-monounsaturated fats is related to health deterioration. Vascular and other diseases and tumours have been directly related to these types of lipids (Stender and Dyerberg, 2004). The deterioration of an organism is manifest in the appearance of these and other types of disease. In this sense, the consumption of specific types of lipids has a clearly positive or negative effect. On the one hand, as described above, saturated or trans-unsaturated fatty acids have negative effects on many physiological parameters, being implicated in lipid changes that give rise to numerous pathologies such as, for example, metabolic pathologies (hypercholesterolemia, hypertriglyceridemia, diabetes, metabolic syndrome, etc.), cancer, cardiovascular pathologies, inflammation, etc. By contrast, cis-monounsaturated and polyunsaturated fatty acids have been related to the prevention of or recovery from these diseases. All these results clearly indicate that lipid changes can cause harmful changes to cell physiology and that regulation of the composition and lipid structure of membranes can reverse these negative changes by coordinated regulation of certain cellular functions.

Thus, changes in the composition and structure of membranes are related to the aetiology of many pathologies and, in many cases, the manifestation of a specific disease is due to the combination of these changes with other changes affecting specific proteins that interact with the membrane or are included in the signal sequence of other proteins interacting with them. Therefore, interventions on the structure and function of biological membranes through the molecules covered by the present invention, can effectively modify certain cellular functions with the net result of reversing specific pathological processes. Given the known relation of changes, both structural and functional, in lipids present in the cellular membrane to the development of various diseases of diverse types, but unitarily related by this aetiology, the present invention is focussed on pharmaceutically acceptable α-derivatives of cis-monounsaturated fatty acids, their salts and derivatives, which are used in the treatment and/or prevention of these diseases. Surprisingly, it is shown in the present invention that the α-derivatives of cis-monounsaturated fatty acids can be successfully used to regulate cell signalling, preventing the appearance of or giving rise to recovery from important diseases.

Patents WO2005041691 and WO2003030891 fundamentally refer to the prevention and treatment of cardiovascular diseases (such as hypertension) and obesity, and to the treatment of lung, brain or prostate cancer by means of the use of compounds of the formula COOH—CHR—$(CH_2)_m$—CH=CH—$(CH_2)_n$—$CH_3$, with cis or trans configurations, where the R group can be substituted by H, OH, $NH_2$ or $CH_3$ or other groups with a molecular weight of less than 200 Da and where the carboxyl group has a hydrogen atom (H). However, the documents of patents WO2005041691 and WO2003030891 do not refer to the use of these same compounds in the prevention of cancer and/or in the prevention and/or treatment of cutaneous pathologies, neurodegenerative pathologies, nerve fibre lesions, pain, inflammatory processes, infectious pathologies or metabolic pathologies such as hypercholesterolemia, hypertriglyceridemia, diabetes or metabolic syndrome. Furthermore, these patents also make no reference to the use of compounds of this formula but where the position R (X in the present invention) can be substituted by different radicals such as F, $F_3C$, HS or O—$CH_3$ in the prevention and/or treatment of cancer, vascular pathologies, cutaneous pathologies, metabolic pathologies, neurodegenerative pathologies, inflammatory processes and infectious pathologies. Also, these patents also do not reveal the use of compounds of this formula but where the position R (X in the present invention) can be substituted by different groups such as, for example: OH, $NH_2$, $CH_3$, F, $F_3C$, HS, O—$CH_3$, $PO_4(CH_2$—$CH_3)_2$ or $CH_3COO$ and position H of the carboxyl group (R in the present invention) can be substituted by different groups such as, for example: sodium (Na), methyl ester (OMe), ethyl ester (EE) or ammonium ($NH_3$) in the prevention and/or treatment of cancer, vascular pathologies, cutaneous pathologies, metabolic pathologies, neurodegenerative pathologies, inflammatory processes and infectious pathologies. Also, these patents also do not reveal the use of compounds of this formula but where the position R (X in the present invention) can be substituted by different groups such as, for example: $PO_4(CH_2$—$CH_3)_2$ or $CH_3COO$ and position H of the carboxyl group (R in the present invention) is retained as H, in the prevention and/or treatment of cancer, vascular pathologies, cutaneous pathologies, metabolic pathologies, neurodegenerative pathologies, inflammatory processes and infectious pathologies. Finally, none of the documents found in the state of the art reveal the use of compounds of this formula but where position R (X in the present invention) can be substituted by different groups such as, for example: OH, $NH_2$, $CH_3$, F, $F_3C$, HS, O—$CH_3$, $PO_4(CH_2$—$CH_3)_2$ or $CH_3COO$ and position H of the carboxyl group (R in the present invention) can be substituted by different groups such as, for example: H, sodium (Na), methyl ester (OMe), ethyl ester (EE) or ammonium ($NH_3$) in the induction of neuroregeneration, prevention and/or treatment of nerve fibre lesions and/or prevention and/or treatment of pain.

So, the higher effectiveness of the isomers with cis configuration is demonstrated in the present invention and new groups have been selected giving rise to compounds that were successfully used in the prevention and/or treatment of diseases where the common aetiology is based on structural and/or functional changes in lipids found in the cellular membrane such as: cancer, vascular pathologies, cutaneous pathologies, metabolic pathologies, neurodegenerative pathologies, nerve fibre lesions, pain, inflammatory processes, HIV and malaria. In addition, as previously referred, the present invention demonstrates new uses for the compounds revealed in patents WO2005041691 and WO2003030891, which are: the prevention and treatment of various types of cancer, cutaneous pathologies, neurodegenerative pathologies, inflammatory processes, infectious pathologies, nerve fibre lesions and pain. Also, new derivatives and combinations of the molecules of the present invention with other active ingredients and excipients have been discovered, in both cases with higher pharmaceutical effectiveness, for the treatment of some pathologies.

None of the documents found in the state of the art refers to the specific use of α-derivatives of cis-monounsaturated fatty acids and their salts in combination treatments with other active ingredients and excipients for the purposes claimed in the present invention. In addition, the particular importance of selecting compounds with the shared structural characteristics of α-derivatives of cis-monounsaturated fatty acids (double link in cis position and specific substitutions in the α-carbon and of the carboxyl group proton and pharmaceutically acceptable related structures) is demonstrated in the present invention so that these can be effectively applied in the treatment of diseases where the aetiology is related to structural and/or functional changes in membrane lipids. Thus, the present invention shows comparative examples where it is demonstrated that other compounds, similar to those used in the present invention but without sharing these structural characteristics, are not as effective as the α-derivatives of cis-monounsaturated fatty acids of the invention.

DESCRIPTION OF THE INVENTION

The present invention refers to α-derivatives of cis-monounsaturated fatty acids and their salts or pharmaceutically acceptable forms to be used as medicines, preferably in the treatment and/or prevention of diseases united by their aetiology that is related to structural or functional changes in membrane lipids. The use of compounds of Formula I, where (X) is replaced by OH, $NH_2$ or $CH_3$ and (R) is replaced by H, for the prevention and treatment of cardiovascular diseases and obesity and for the treatment of lung, brain or prostate cancer in humans, is excluded.

The diseases or pathologies that are linked by their common aetiology, and prevented or treated by means of the use of α-derivatives of cis-monounsaturated fatty acids of the invention are, for example:

Cancer (see Table 2): prostate cancer, breast cancer, pancreas cancer, leukaemia, cervical cancer, colon cancer, brain cancer, lung cancer.
Vascular pathologies: arteriosclerosis, cardiomyopathies, angiogenesis, cardiac hyperplasia and hypertension.
Cutaneous pathologies: cellulite, vitiligo and psoriasis.
Metabolic pathologies: hypercholesterolemia, hypertriglyceridemia, diabetes, metabolic syndrome and obesity.
Neurodegenerative pathologies: Alzheimer's disease, Parkinson's disease and sclerosis.
Inflammatory processes that result in pain, cardiovascular diseases, systemic diseases, ageing, respiratory diseases and rheumatoid arthritis.
Infectious pathologies: AIDS and malaria.
Nerve fibre lesions: pathologies related to neuronal damage, abnormal voluntary motor function with or without corticospinal tract dysfunction or extrapyramidal motor paralysis, spasticity resulting from spinal cord injury with or without a component of central sensitization, etc. The compounds of the invention are, therefore effective in inducing neuroregeneration.
Pain caused by damage to the central nervous system: processes that require analgesia, neuropathic pain, changes in nociperception, etc.

The α-derivatives of cis-monounsaturated fatty acids used in the present invention for this purpose (hereinafter called fatty acids of the invention) belong to structural group 1 shown in Table 1 and to the compounds of Table 5 and are characterised by having the general Formula (I):

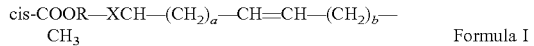

where (a) and (b) can take any value between 0 and 14, (X) linked to the α-carbon atom can be substituted by any atom or group of atoms with an atomic/molecular weight between 4 and 200 Da and (R) can be substituted by any atom or group of atoms with an atomic/molecular weight between 1 and 200 Da, both (X) and (R) selected, for example, from: alcohols, organic acids, alkyl groups, amino groups, halogens, alkyl halogens, alkyloxy groups and mercapto groups.

In a particular embodiment of the invention, radical (X) can be substituted by a group selected from: OH, $NH_2$, $CH_3$, F, $F_3C$, HS, O—$CH_3$, $PO_4(CH_2—CH_3)_2$ and $CH_3COO$.

In another particular embodiment of the invention, radical (R) can be substituted by: H, sodium (Na), a methyl ester (OMe), an ethyl ester (EE), ammonium ($NH_3$) and any other radical that makes a salt or pharmaceutically acceptable form of the compounds of Formula I.

For effective functioning of this structure, the double bond (═) in the cis configuration and these substitutions on the α-carbon are essential. Trials carried out with molecules analogous to those described in Formula I but lacking the substitutions on the α-carbon atom (X is a hydrogen atom), having a trans double bond or lacking the double bond (saturated fatty acids), showed a lower prevention or curative activity with respect to that shown by the fatty acids of the invention.

Different salts of the molecules of the invention have been studied (Table 5). Their effectiveness is, in some cases, significantly better than those of the free fatty acids. This effect may be due to improvements in absorption of the compounds or in their distribution. Thus, substitution of the hydrogen of the carboxyl group (R) has been demonstrated in the present invention to give rise to certain salts or derivatives that showed pharmacologically better activity that the free fatty acids themselves. For example, the sodium salt, in which R is substituted by Na, induces greater reductions in tumour volumes than the form in which R is substituted by H, so the sodium salt would be one of the preferred choices for the preparation of a pharmaceutical or nutraceutical composition for the prevention or treatment of cancer.

Certain peripheral signalling proteins involved in the propagation of messages to the interior of cells can be anchored in regions where the packing of the surface is loose (FIG. 1). Fatty acids that are unsaturated in cis configuration and with substitutions in the α-carbon different to substitutions by H, are located in the membrane (either in their free form or forming part of larger structures such as phospholipids), causing discontinuities in the packing of the polar heads of the phospholipids found on the surface of the cell barrier where protein-G, PKC and Ras-type proteins may bind. By contrast, saturated or trans-monounsaturated fatty acids prevent the attachment of these proteins to the membranes, interfering with cell signalling. This does not imply that saturated fatty acids must be removed from the diet but that the levels of consumption of these lipids, present in standard diets in countries with average to high development levels, are higher than those required by the cells to perform their functions properly. In fact, the various lipid microdomains (e.g. "lipid rafts") that appear in membranes are spaciotemporal platforms where proteins with affinity for these domains (based on protein-lipid interactions) may gather and can have productive interactions enabling the propagation of cellular signals. Any change in the density or structure of these domains has consequences on cellular signalling, so that pharmaceutical and nutraceutical interventions leading to regulation of membrane lipids can be more or less effective than those targeting proteins or nucleic acids directly.

The broad spectrum of therapeutic application offered by the fatty acids of the invention is demonstrated by various phenomena. Firstly, ingestion of lipids with negative effects (saturated and trans-monounsaturated fats) or positive effects (cis-monounsaturated fats) affect all the cells of the organism in a similar way so that their effects, both negative and positive, are shown in many ways: induction or reduction in obesity, hypertension, cancer, etc. When a particular type of lipid is ingested, it is distributed throughout the organism and gives rise to regulation of the lipid species in cellular membranes of all organs. Changes in the levels of lipids as a consequence of specific physiological or pathological processes (such as acclimatisation to cold water in poikilothermic fish) affect practically all the cells of the organism (Buda et al., 1994). Finally, fatty acids can be stored or degraded to produce energy. In fact, these molecules are exceptional cellular fuels so that the direct use of unmodified fatty acids has a modest impact on health. However, blocking their degradation, by the addition of modifications to the α-carbon atom, allows these molecules to persist for a long time, both in the cytoplasm and in the membranes, thus allowing their therapeutic action. In this sense it has been shown that the plasma levels of α-derivatives of cis-monounsaturated fatty acids are maintained at high levels one hour after being injected (50-60% of initial levels), whereas natural fatty acids have practically disappeared after this period (levels of 2-4%). Therefore, α-derivatives of cis-monounsaturated fatty acids used in the present invention cause a broad range of positive effects without observable secondary effects. To demonstrate that only fatty acids that are unsaturated in the cis conformation and with a substitution on the α-carbon with an atom other than H, and not other similar structures, have therapeutic properties at various levels, different types of fatty acids (see Table 1) belonging to different structural groups (1-4) were tested in the present invention: α-derivatives of cis-mono-unsaturated fatty acids (fatty acids of the invention) (1), fatty acids with a double bond in cis configuration but without modifications on the α-carbon other than to H (2), fatty acids with the α-carbon substituted by radicals other than H but without a double bond in cis configuration (3), fatty acids without a double bond in cis configuration and without substitutions in the α-carbon other than H (4).

The mechanism of action of these molecules (based on the regulation of the composition and structure of biological membranes) is different to the majority of pharmaceuticals used for treating human pathologies (based on the interaction with proteins, in the majority of cases, or nucleic acids). Therefore, they can be used in combinatory therapies in which one of the compounds of the present invention is used in addition to at least another molecule (active ingredient and/or excipient), and the combined therapy can be much more effective than a monotherapy with just one of the compounds. In the present invention it is demonstrated, for example, that OHOD combined with any of the anti-tumour pharmaceuticals studied (temozolomide, erlotinib, gemcitabine, cisplatin) has a higher therapeutic effect than any of the compounds used separately.

The broad spectrum of therapeutic application offered by the fatty acids of the invention allows the general assumption that lipids with the cis-monounsaturated structure confer specific structural properties enabling proper activity of the processes carried out in and by these membranes. In other words, the fatty acids of the invention can be effectively used for the prevention and/or treatment of any disease where the aetiology is related either to changes in the levels, composition, structure or any other type of changes to biological membrane lipids or to altered regulation of cellular signalling as a result of these changes in the lipids present in biological membranes.

Therefore, the present invention refers to a compound of Formula I: pharmaceutically acceptable cis-COOR—XCH—$(CH_2)_a$—CH═CH—$(CH_2)_b$—$CH_3$, its salts and its derivatives, where (a) and (b) can take any value between 0 and 14, (X) can be substituted by any atom or group of atoms with an atomic/molecular weight between 4 and 200 Da and (R) can be substituted by any atom or group of atoms with an atomic/molecular weight between 1 and 200 Da, both (X) and (R) being selected from: alcohols, organic acids, alkyl groups, amino groups, halogens, alkyl halogens, alkyloxy groups and mercapto groups, to be used independently or in combination with other compounds, as medicines in humans and animals; excluding compounds of Formula I where (R) is H and (X) is substituted by OH, $NH_2$ or $CH_3$ for the prevention and treatment of cardiovascular diseases and obesity, and for the treatment of lung, brain and prostate cancer.

In a preferred embodiment, (X) is substituted by a group selected from: OH, $NH_2$ and $CH_3$, and (R) is substituted by H, in Formula I, giving rise to compounds for use in the prevention of cancer and/or in the prevention and/or treatment of cutaneous pathologies, neurodegenerative pathologies, inflammatory processes, infectious pathologies or metabolic pathologies such as hypercholesterolemia, hypertriglyceridemia, diabetes or metabolic syndrome.

In another preferred embodiment, (X) is substituted by a group selected from: F, $F_3C$, HS and O—$CH_3$ and (R) is substituted by H in Formula I, giving rise to compounds for use in the prevention and/or treatment of cancer, vascular pathologies, cutaneous pathologies, metabolic pathologies, neurodegenerative pathologies, inflammatory processes and infectious pathologies.

In another preferred embodiment, (X) is substituted by a group selected from: OH, $NH_2$, $CH_3$, F, $F_3C$, HS, O—$CH_3$, $PO_4(CH_2—CH_3)_2$ and $CH_3COO$ and (R) can be substituted by sodium (Na), methyl ester (OMe), ethyl ester (EE) or ammonium ($NH_3$) in Formula I, giving rise to compounds for use in the prevention and/or treatment of cancer, vascular pathologies, cutaneous pathologies, metabolic pathologies, neurodegenerative pathologies, inflammatory processes and infectious pathologies.

In another preferred embodiment, (X) is substituted by a group selected from: $PO_4(CH_2—CH_3)_2$ and $CH_3COO$ and (R) is substituted by H in Formula I, giving rise to compounds for use in the prevention and/or treatment of cancer, vascular pathologies, cutaneous pathologies, metabolic pathologies, neurodegenerative pathologies, inflammatory processes and infectious pathologies.

In another preferred embodiment, (X) is substituted by a group selected from: OH, $NH_2$, $CH_3$, F, $F_3C$, HS, O—$CH_3$, $PO_4(CH_2—CH_3)_2$ and $CH_3COO$ and (R) is substituted by a group selected from: H, sodium (Na), methyl ester (OMe), ethyl ester (EE) or ammonium ($NH_3$) in Formula I for use in the induction of neuroregeneration, prevention and/or treatment of nerve fibre lesions and/or prevention and/or treatment of pain.

In another preferred embodiment, the compounds of Formula I are: OHHD, OHOD, MOD, AOD, FOD, TFMOD, MOOD, SHOD, MOD11, OHOD11, OHEE, OHDE, Na—OHOD, OMe-OHOD, EE-OHOD, $NH_3$—OHOD, ACOD, Na-ACOD, OMe-ACOD, EE-ACOD, Na-MOOD, OMe-MOOD, EE-MOOD, DEPOD, Na-DEPOD, OMe-DEPOD and EE-DEPOD.

As previously described, the compounds can be used in combination with other active ingredients or excipients to give rise to pharmaceutical and/or nutraceutical compositions useful in the prevention and/or treatment of cancer, vascular pathologies, cutaneous pathologies, metabolic pathologies, neurodegenerative pathologies, inflammatory processes or infectious pathologies and/or for the induction of neuroregeneration, prevention and/or treatment of nerve fibre lesions and/or prevention and/or treatment of pain.

Thus the fatty acids of the invention can be administered independently or formulated in pharmaceutical or nutraceutical compositions where they are combined with excipients such as, for example: binders, fillers, disintegrants, lubricants, coaters, sweeteners, flavourings, colourings, carriers, etc., and combinations thereof. Also, the fatty acids of the invention can form part of pharmaceutical or nutraceutical compositions in combination with other active ingredients. For the purposes of the present invention, the term nutraceutical is defined as a compound that is ingested periodically during feeding or as a food complement and that serves to prevent or reverse diseases, in this case diseases where the aetiology is linked to changes in the lipids of the cellular membrane.

The administration of the fatty acids of the invention can be performed by any route such as, for example, enteral (by the digestive tract), oral (pills, capsules, powders, emulsions, tablets or syrups), rectoral (suppositories or enemas), topical (creams or patches), inhalation, parenteral injection, intravenous injection, intramuscular injection or subcutaneous injection, in the form indicated above or in any pharmaceutically acceptable form such as, for example: methyls, ethyls, phosphates, other ester-type radicals, ethers, alkyls, etc.

Therefore, the present invention, also refers to a pharmaceutical and/or nutraceutical composition that comprises a compound of Formula I, where (a) and (b) can take any value between 0 and 14, (X) can be substituted by any atom or group of atoms with an atomic/molecular weight between 4 and 200 Da and (R) can be substituted by any atom or group of atoms with an atomic/molecular weight between 1 and 200 Da and, at least one second compound with therapeutic or excipient activity.

In a preferred embodiment of the invention, this excipient formulated in combination with the compounds of the invention is albumin, for example: ovalbumin, lactalbumin, native or recombinant albumin of human, bovine, murine or rabbit origin, more preferably human serum albumin or bovine serum albumin. Thus, the composition comprising a fatty acid of the invention and albumin is effective in the prevention and treatment of the indications listed above, preferably in the induction of neuroregeneration, prevention and/or treatment of nerve fibre lesions and/or prevention and/or treatment of pain. In a preferred embodiment, the composition comprises OHOD or any of its derivatives such as, for example Na—OHOD, and albumin.

The composition comprising a fatty acid of the invention and another active ingredient is effective in the prevention and treatment of the indications listed above, preferably in the prevention and/or treatment of cancer when the active ingredient is an anti-cancer compound. In a preferred embodiment, the composition comprises OHOD and/or Na—OHOD and an anti-cancer compound selected, for example, from: temozolomide, erlotinib, gemcitabine and cisplatin.

Another aspect of the present invention refers to a cosmetic, not therapeutic, method for improving cutaneous appearance comprising the administration on the skin of an effective quantity of at least one pharmaceutically or cosmetically acceptable compound of Formula I and/or its salts or derivatives, where (a) and (b) can take any value between 0 and 14, (X) can be substituted by any atom or group of atoms with an atomic/molecular weight between 4 and 200 Da and (R) can be substituted by any atom or group of atoms with an atomic/molecular weight between 1 and 200 Da, selected from: alcohols, organic acids, alkyl groups, amino groups, halogens, alkyl halogens, alkyloxy groups and mercapto groups.

Finally, the present invention refers to a method for the prevention and/or therapeutic treatment of diseases in humans and animals, where the common aetiology is related to structural and/or functional changes in lipids of the cellular membrane, that comprises the administration to the patient of a therapeutically effective amount of at least one pharmaceutically acceptable compound of Formula I, independently or in combination with other compounds, of its salts or derivatives, where (a) and (b) can take any value between 0 and 14, (X) can be substituted by any atom or group of atoms with an atomic/molecular weight of between 4 and 200 Da and (R) can be substituted by any atom or group of atoms with an atomic/molecular weight between 1 and 200 Da, both (X) and (R) being selected from: alcohols, organic acids, alkyl groups, amino groups, halogens, alkyl halogens, alkyloxy groups and mercapto groups; excluding the administration of compounds of Formula I where (R) is H and (X) is substituted by OH, NH$_2$ or CH$_3$ for the prevention and treatment of cardiovascular diseases and obesity, and for the treatment of lung, brain and prostate cancer.

For the purposes of the present invention, the term "therapeutically effective amount" is understood to be that amount that reverses the disease or prevents it without showing adverse secondary effects, or in the case that such effects are caused they are acceptable according to the criteria defined by the pharmaceutical regulatory agencies (basically where the benefit is higher than the harm caused; e.g. episodes of nausea being acceptable in a patient with a cancer with a serious prognosis).

DESCRIPTION OF THE FIGURES

FIG. 4A. Cancer cells (A549) were incubated in the absence of OHOD. Then they were fixed, incubated in the presence of an antibody against cadherin and were observed by confocal microscopy.

FIG. 4B. Cancer cells (A549) were incubated in the presence of OHOD (100 μM, 48 h). Then they were fixed, incubated in the presence of an antibody against cadherin and were observed by confocal microscopy. Treatments with 50 μM OHOD (48 h) induced an increase of 73.6±5.4% in the levels of this protein. In treatments with the fatty acids of the invention, a significant increase in cadherin levels was observed.

FIG. 5A. Invasive capacity of lung cancer cells (A549) in culture, in the absence (control, C) or presence of OHOD (2-hydroxy-9-cis-octadecenoic acid) at 50 μM (M50) and 100 μM (M100) and at different times. Lung cancer cells cultivated in the presence of OHOD had a lower invasive capacity to those shown by untreated cells (C) ($p<0.05$). These results indicate that the fatty acids of the invention can be used to prevent or treat the development of tumour metastasis.

FIG. 5B. Invasive capacity of lung cancer cells (A549) in culture, in the absence (control, C) or presence of OHOD (2-hydroxy-9-cis-octadecenoic acid) at 50 μM (M50) and 100 μM (M100) and at different times. Lung cancer cells cultivated in the presence of OHOD had a lower invasive capacity to those shown by untreated cells (C) ($p<0.05$). These results indicate that the fatty acids of the invention can be used to prevent or treat the development of tumour metastasis. FIG. 5B shows the number of invasive cells on the vertical axis and the time in hours on the horizontal axis.

Rats treated with Albumin-OHOD (4 mM, 10 µl by intrathecal route) showed a greater inhibition of the temporal summation of the plantar withdrawal reflex of the tibialis anterior 28 days after nerve fibre lesion compared to rats treated with saline or with Albumin-Oleic acid. These results suggest that Albumin-OHOD complexes are highly effective in the treatment of acute and chronic pain.

Figure 18:
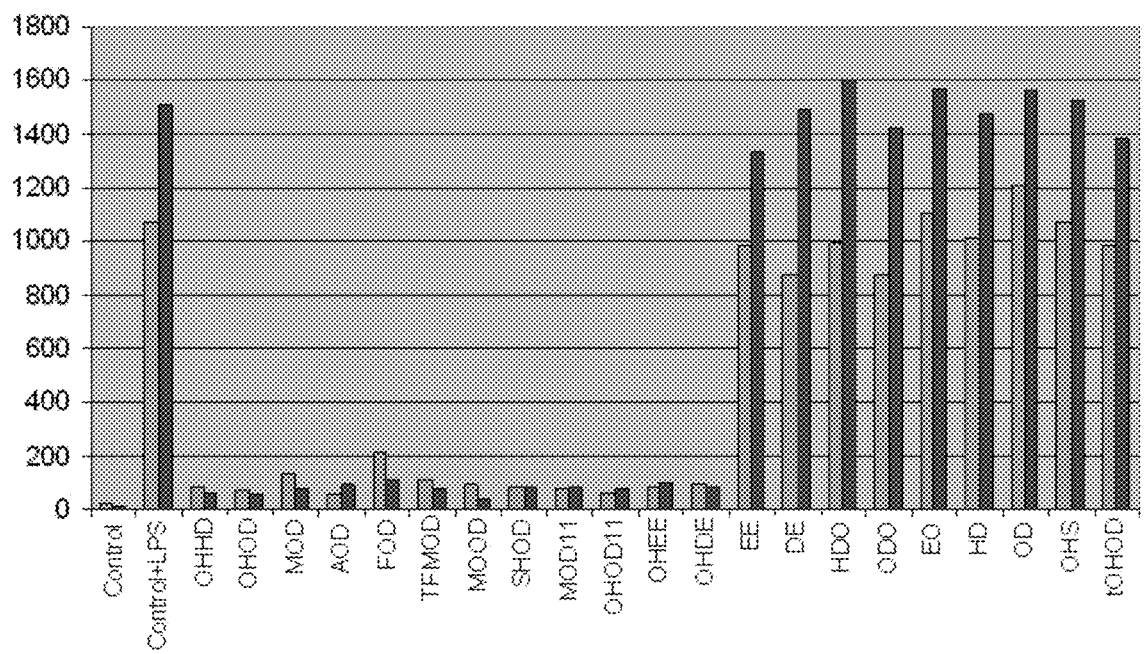

FIG. 18. Levels of interleukin 6 IL-6 (left bar) and transcription factor TNF-α (right bar) in human monocytes in the absence (control) or presence of a pro-inflammatory treatment with bacterial lipopolysaccharide (LPS). Cells treated with LPS were cultured in the absence (Control+LPS) or presence of various fatty acids shown on the horizontal axis. In a cellular inflammation model (U937 monocytes in culture stimulated with bacterial lipopolysaccharide, LPS) the fatty acids of the invention (250 µM, 72 h) significantly inhibited the expression of the most important proinflammatory cytokines (IL-6 and TNF-α, p<0.05).

Figure 19A:
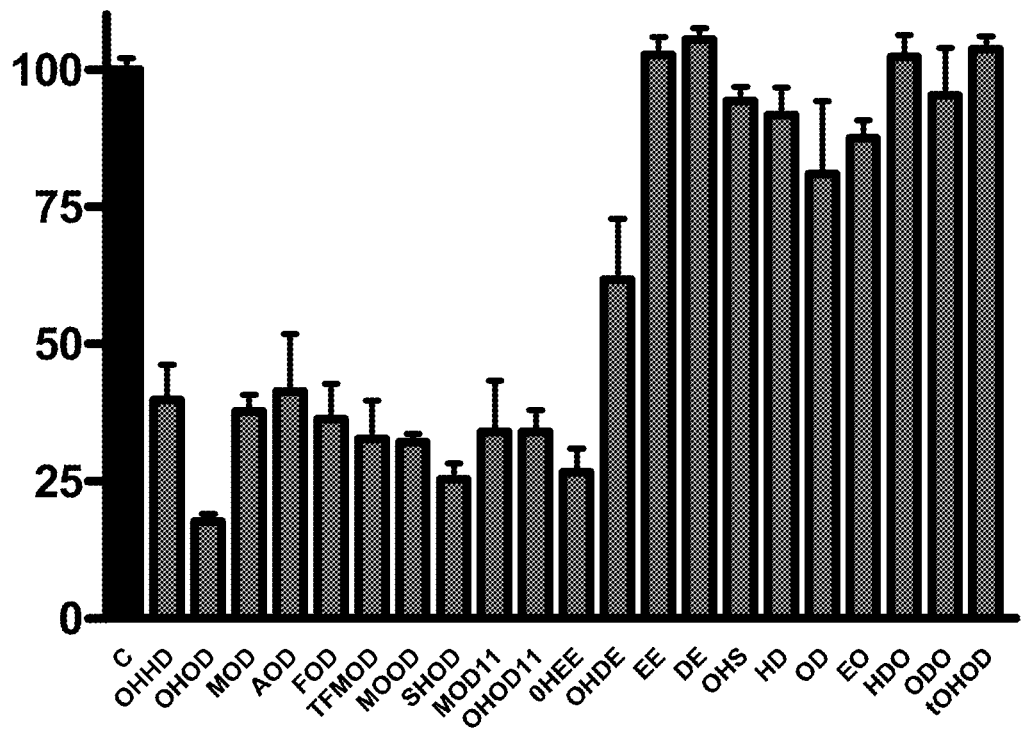

FIG. 19A. Effect of various fatty acids in the inhibition of the activity of cyclooxygenases-1 (COX-1) (Cayman COX-1 inhibitor screening system). The horizontal axis shows the type of fatty acid used and the vertical axis shows the COX-1 activity (% of control). Cell cultures (U937 differentiated monocytes) were treated with the fatty acids of the invention (250 µM, 6 hours). The vertical axis shows the COX-1 activity after treatment. The fatty acids of the invention (OHHD, OHOD, MOD, AOD, FOD, TFMOD, MOOD, SHOD, MOD11, OHOD11, OHEE and OHDE) were observed to have a more significant effect (p<0.05 in all cases) than cis-monounsaturated fatty acids without derivation in the α-position (EE, DE, HOD, ODO), than saturated fatty acids of identical length (HD, OD, EO), and the α-derivatives of fatty acids that were not cis-monounsaturated (OHS, tOHOD).

Figure 19B:
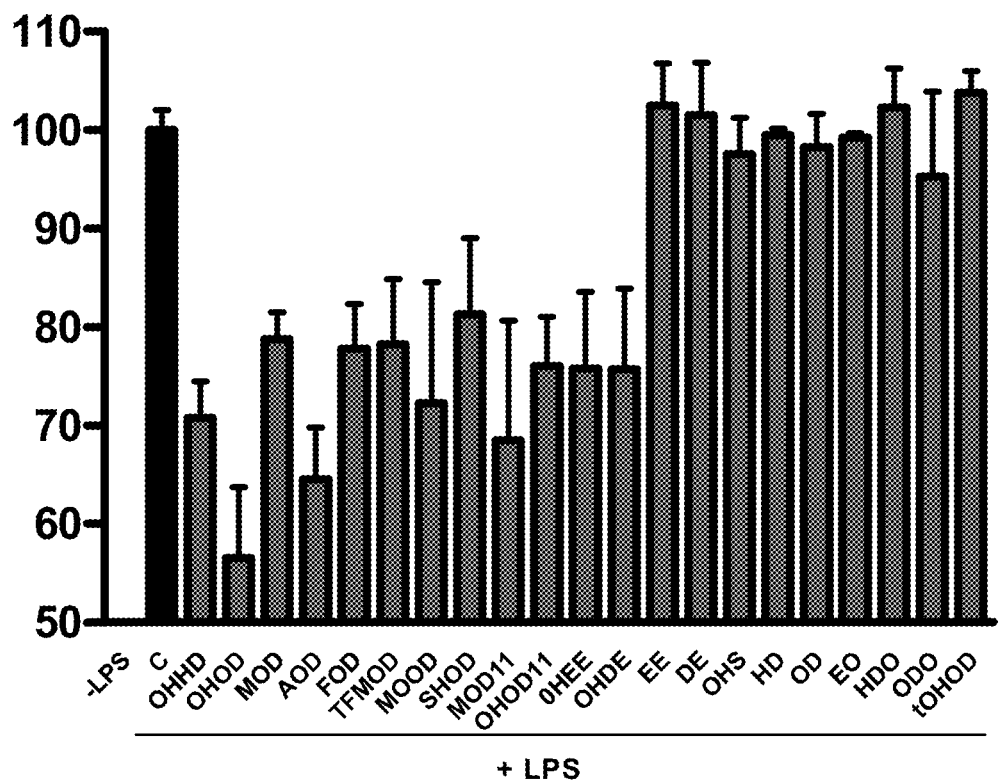

FIG. 19B. Effect of various fatty acids in the inhibition (concentration of protein) of cyclooxygenase-2 (immunoblot of COX-2). The horizontal axis shows the type of fatty acid used and the vertical axis shows the cellular concentration of COX-2 (% of control). Cell cultures (U937 differentiated monocytes) were treated with the fatty acids of the invention (250 µM, 6 hours). The fatty acids of the invention (OHHD, OHOD, MOD, AOD, FOD, TFMOD, MOOD, SHOD, MOD11, OHOD11, OHEE and OHDE) were observed to have a more significant effect (p<0.05 in all cases) than cis-monounsaturated fatty acids without derivation in the α-position (EE, DE, HOD, ODO), than saturated fatty acids of identical length (HD, OD, EO), and the α-derivatives of fatty acids that were not cis-monounsaturated (OHS, tOHOD).

fatty acids of the invention induced a very marked reduction of this enzyme so they have a significant activity in the prevention and/or treatment of malaria and other infectious processes.

TABLE 1

| Fatty Acid | Series | Abbreviation | Structural group | (a), (b) | (X) |
|---|---|---|---|---|---|
| α-Hydroxy-cis-Δ9-hexadecenoic | 16:1 | OHHD | 1 | 4, 7 | OH |
| α-Hydroxy-cis-Δ9-octadecenoic | 18:1 | OHOD | 1 | 6, 7 | OH |
| α-Methyl-cis-Δ9-octadecenoic | 18:1 | MOD | 1 | 6, 7 | CH$_3$ |
| α-Amino-cis-Δ9-octadecenoic | 18:1 | AOD | 1 | 6, 7 | NH$_2$ |
| α-Fluoro-cis-Δ9-octadecenoic | 18:1 | FOD | 1 | 6, 7 | F |
| α-Trifluoromethyl-cis-Δ9-octadecenoic | 18:1 | TFMOD | 1 | 6, 7 | F$_3$C |
| α-Methoxy-cis-Δ9-octadecenoic | 18:1 | MOOD | 1 | 6, 7 | O—CH$_3$ |
| α-Mercapto-cis-Δ9-octadecenoic | 18:1 | SHOD | 1 | 6, 7 | HS |
| α-Methyl-cis-Δ11-octadecenoic | 18:1 | MOD11 | 1 | 4, 9 | CH$_3$ |
| α-Hydroxy-cis-Δ11-octadecenoic | 18:1 | OHOD11 | 1 | 4, 9 | OH |
| α-Hydroxy-cis-Δ11-eicosenoic | 20:1 | OHEE | 1 | 6, 9 | OH |
| α-Hydroxy-cis-Δ13-docosenoic | 22:1 | OHDE | 1 | 6, 11 | OH |
| Cis-Eicosenoic | 20:1 | EE | 2 | 6, 9 | — |
| Cis-Docosenoic | 22:1 | DE | 2 | 6, 11 | — |
| α-Hydroxy-octadecanoic | 18:0 | OHS | 3 | — | OH |
| Trans-Hexadecenoic | 16:1 | HD | 2 | 4, 7 | — |
| Trans-Octadecenoic | 18:1 | OD | 4 | 6, 7 | — |
| Eicosanoic | 20:0 | EO | 4 | — | — |
| Hexadecanoic | 16:0 | HDO | 4 | — | — |
| Octadecanoic | 18:0 | ODO | 4 | — | — |
| α-Hydroxy-trans-octadecenoic | 18:1 | tOHOD | 3 | 6, 7 | OH |

(1) α-derivatives of cis-monounsaturated fatty acids (fatty acids of the invention).
(2) fatty acids with a double bond in cis configuration but without modifications on the α-carbon.
(3) fatty acids with a modified α-carbon but without a double bond in cis configuration.
(4) fatty acids without a double bond in cis configuration and without modifications on the α-carbon.

Figure 20:
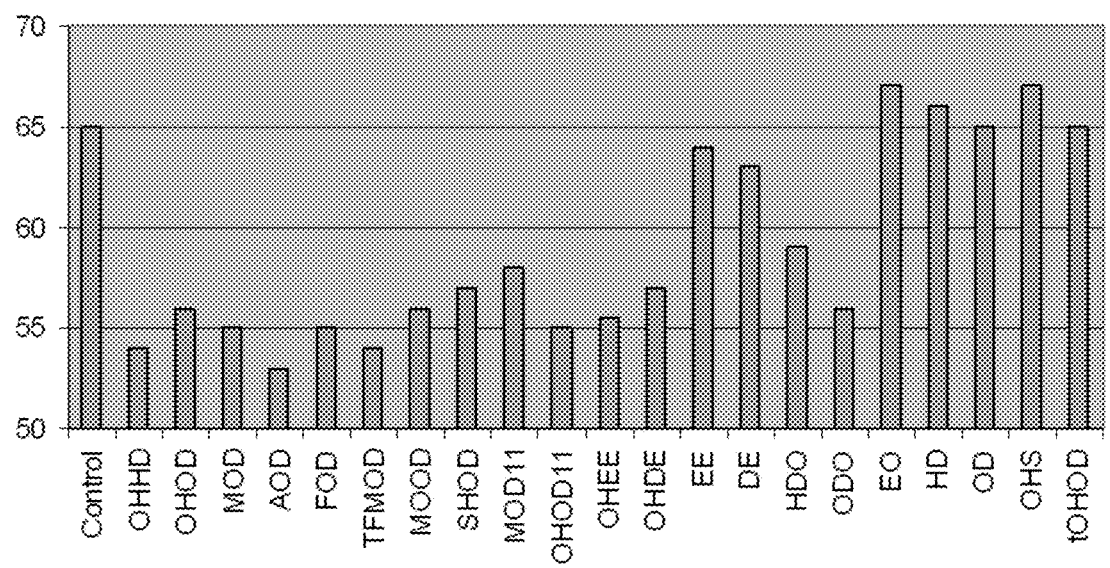

FIG. 20. Lamellar-hexagonal phase transition temperature in model membranes of dielaidoyl phosphatidylethanolamine (DEPE) measured by differential scanning calorimetry. The fatty acids used are shown on the horizontal axis and the temperature is shown on the vertical axis. The higher the change in this transition temperature, the higher capacity to regulate the structure of the membrane, such as that which surrounds human cells or the AIDS virus. The fatty acids of the invention (proportion of fatty acid:DEPE 1:20, mol:mol) induced significant reductions (p<0.05 in all cases) in the lamellar-hexagonal transition temperature.

Figures 21A, 21B:
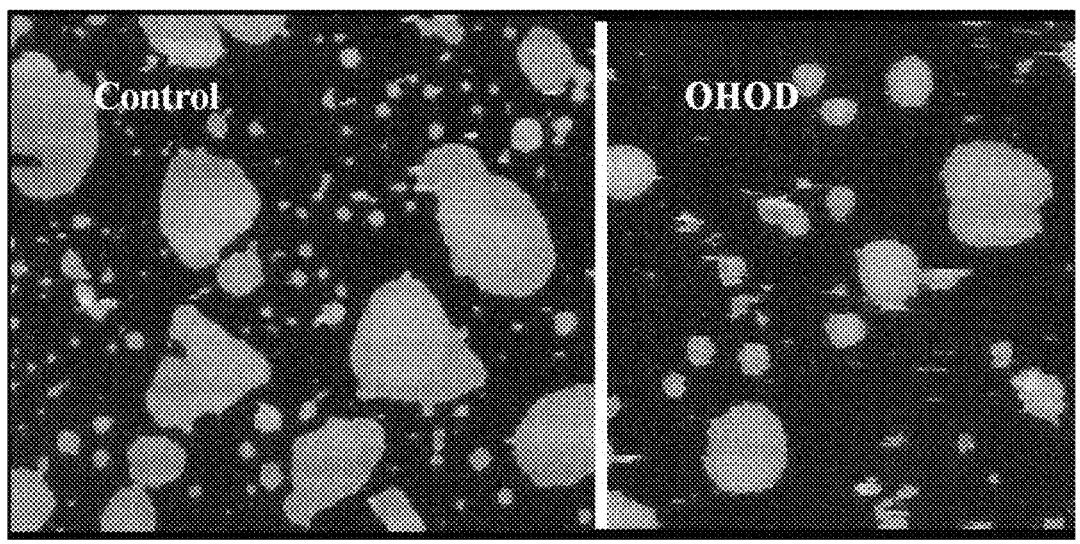

FIG. 21A. Example representative of the effect of the fatty acids of the invention on the "membrane raft". Model membranes of Sphingomyelin/Phosphatidylcholine/Cholesterol (membrane raft model) in the absence of OHOD.

FIG. 21B. Example representative of the effect of the fatty acids of the invention on the "membrane raft". Model membranes of Sphingomyelin/Phosphatidylcholine/Cholesterol (membrane raft model) in the presence of OHOD. The presence of this fatty acid induced a reduction in the surface occupied by the membrane rafts and their average size.

Figure 21C:
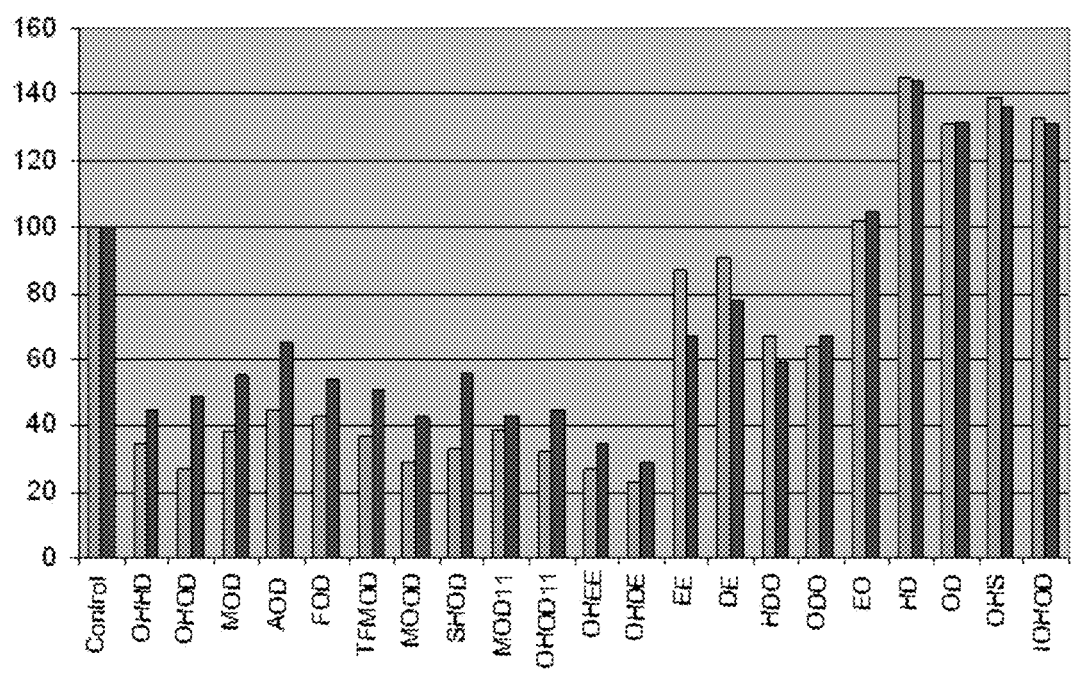

FIG. 21C. The graph shows the quantification of the effect of various fatty acids on the total surface area of membrane rafts (or ordered lamellar regions of membrane, Lo, left column) compared to Ld regions (disordered lamellar regions of membrane; a value of 100% was assigned to control membranes) and the average size (average diameter) of the membrane rafts (right column), in Sphingomyelin/Phosphatidylcholine/Cholesterol membranes. The fatty acids of the invention regulate the structure of the "lipid rafts" by interfering in the virus-cellular interaction necessary to cause and amplify virus infection.

Figure 22:
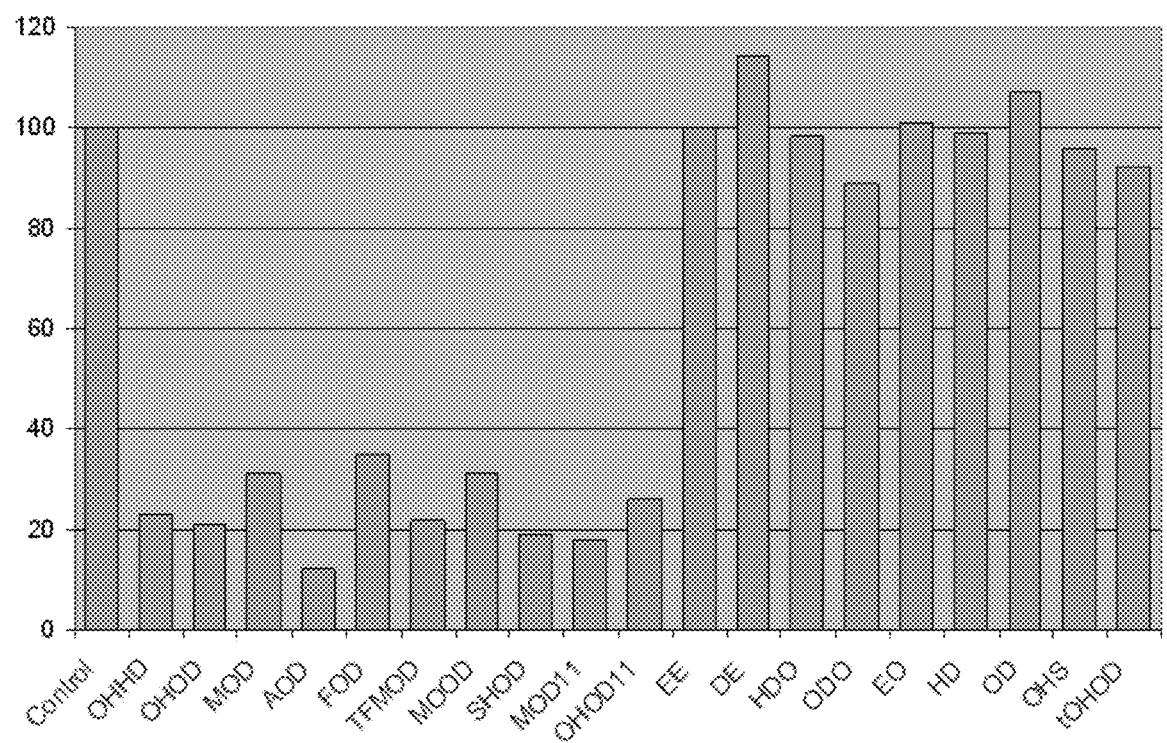

FIG. 22. Levels of DHFR (Dihydrofolate Reductase) in A549 cells after treatments with various fatty acids (horizontal axis) at a concentration of 100 μM for 48 hours. The

EXAMPLES

Example 1

Figure 1:
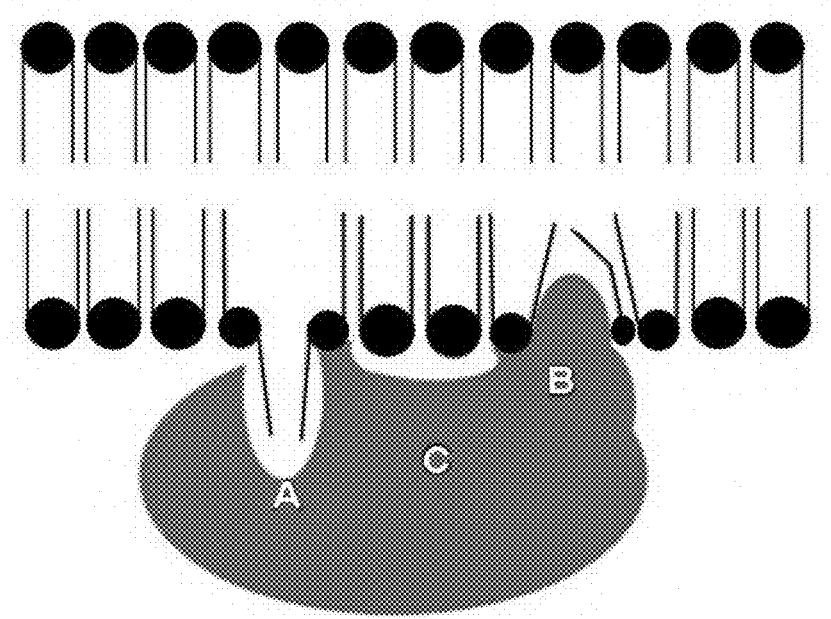
FIG. 1. Binding of cellular signalling proteins to cellular membranes. The peripheral signalling proteins (A, B and C) are bound to membranes through one or several mechanisms such as specific interaction with membrane lipids, electrostatic interactions and/or insertion of hydrophobic regions into areas of high non-lamellar propensity, mediated by cis-monounsaturated lipids. Therefore, α-derivatives of cis-monounsaturated fatty acids can regulate the interaction of certain membrane and cellular signalling proteins.
Figure 2:
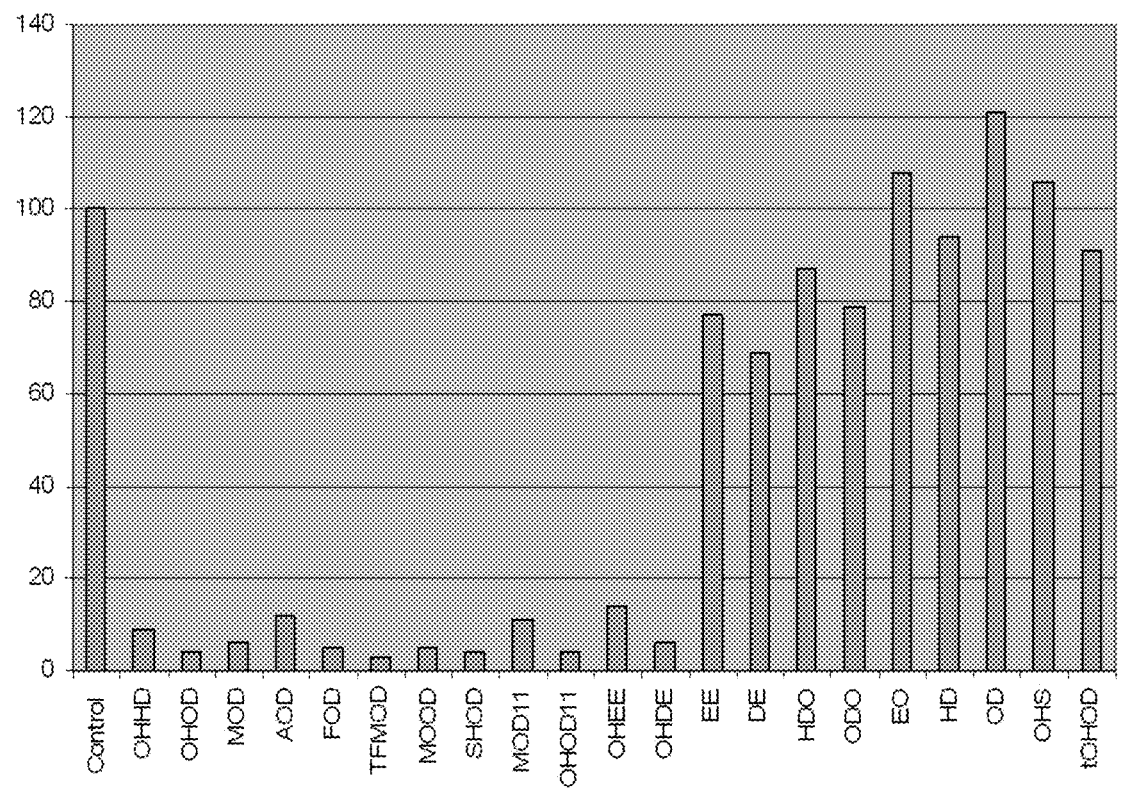
FIG. 2. Preventative effect of various fatty acids against tumour development. The horizontal axis shows the type of fatty acid used for the prevention of cancer development and the vertical axis shows the tumour volume. Animals received treatment before injection of tumour cells and the treatment was subsequently maintained. Animals of the control group were not treated and the volume of their tumours was taken as the reference value (100%). The fatty acids of the invention (OHHD, OHOD, MOD, AOD, FOD, TFMOD, MOOD, SHOD, MOD11, OHOD11, OHEE and OHDE) had a more significant effect ($p<0.05$ in all cases) than cis-monounsaturated fatty acids without derivation in the α-position (EE, DE, HOD, ODO), than saturated fatty acids of identical length (HD, OD, EO), and the α-derivatives of fatty acids that were not cis-monounsaturated (OHS, tOHOD) (see Table 1).

Use of the Fatty Acids of the Invention and of Their Salts for the Prevention and/or Treatment of Cancer To determine whether the fatty acids of the invention have applications in the prevention of the development of tumour processes, an animal cancer model was used. This model consisted of immune-deprived animals ([Crl:Nu(Ico)-Fox1] nude mice in which non-microcytic human lung cancer cells were injected (5×10$^6$ A549 cells per animal). The control group (infected with cancer cells but untreated) started to develop tumours that were visible after a few days. The sizes of the tumours were measured for the first time at 10 days after implanting the tumour and measurements continued for up to 31 days after the implantation with a digital calliper. The volume of the tumours was calculated with the following equation:

$$v = w^2 \times l/2$$

where v is the volume of the tumour, w is its width and l is the length. Preventative treatments against development of the cancer were applied. To carry out these treatments, 400 mg/kg were administered per day for 2 weeks before the injection of tumour cells. This treatment was continued for one month after the implantation of the tumour cells and the volume of the tumours in the animals was measured. Each experimental group was composed of 8 animals. Oral administration of α-derivatives of cis-monounsaturated fatty acids prevented cancer development (A549 cells of human lung adenocarcinoma) (FIG. 2). However, the administration of saturated or trans-monounsaturated fatty acids (both natural and α-derivatives) did not prevent the appearance of cancer in laboratory animals. Therefore it was concluded that the introduction of a double bond in the cis configuration in the structure of the fatty acid is a critical factor in the prevention and treatment by fatty acids of cancer development. Also, the presence of a modification on the α-carbon significantly and very markedly increased the effectiveness of prevention and treatment of cancer development by monounsaturated fatty acids (FIG. 2). In this sense, the α-derivatives of cis-monounsaturated fatty acids (OHHD, OHOD, MOD, AOD, FOD, TFMOD, MOOD, SHOD, MOD11, OHEE and OHDE) had a more marked effect than cis-monounsaturated fatty acids without derivatives in the α-position (EE, DE, HOD, ODO), saturated fatty acids of identical length (HD, OD, EO), or α-derivatives of fatty acids that were not cis-monounsaturated (OHS, tOHOD) (see Table 1).

Figure 3A:
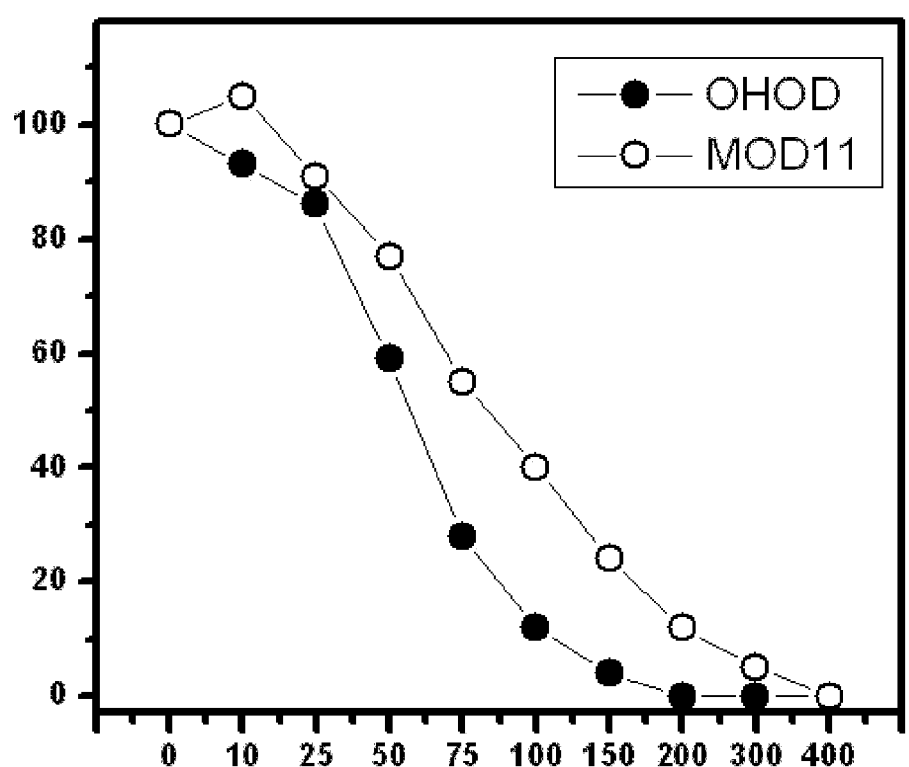
FIG. 3A. Cancer cells (A549) were treated with various concentrations of OHOD and MOD11 to determine whether the effect was dependent on the concentration. The horizontal axis shows the μM concentration of fatty acids used and the vertical axis shows the viability of untreated A549 cells (% control). These cells were treated with different concentrations (0-400 μM) of OHOD and MOD11 and the number of cells was determined by flow cytometry. Both compounds reduced the growth of tumour cells, showing values of IC$_{50}$ (concentration reducing the number of viable cells to 50%) in the range of 50 to 100 μM after 48 hours of incubation. Doses of 200 to 400 μM resulted in total elimination of tumour cells in all cases.
Figure 3B:
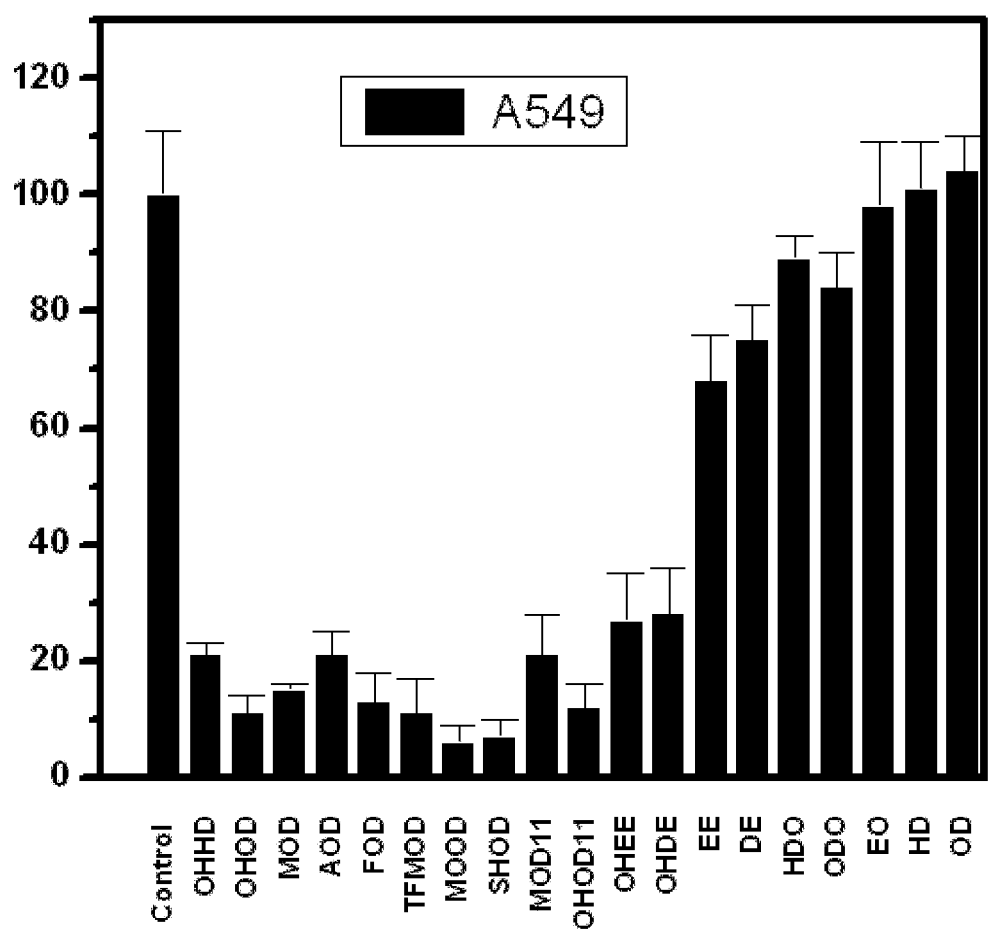
FIG. 3B. Cancer cells (A549) were treated with compounds indicated on the horizontal axis for 48 hours at 150 μM. Then, the cells were counted and their number and percent of untreated (control) represented on the vertical axis. In these cultures, incubation with 150 μM of fatty acids of the invention caused an inhibition of tumour cell growth ($p<0.05$ in all cases), indicating that these are effective molecules for the treatment of cancer.

Also, a series of α-derivatives of cis-monounsaturated fatty acids were used to investigate their effectiveness in cancer treatment. Two types of experiment were performed. Firstly, the dependency of the anti-tumour effect on concentration was investigated. To perform these experiments, human lung cancer cells (A549) were cultivated in RPMI medium, supplemented with 10% foetal bovine albumin, 10 mM Hepes (pH 7.4), 2 mM glutamine, 2 g/l bicarbonate, 1 g/l glucose, 100 units/ml penicillin, 0.1 mg/ml streptomycin, 0.25 µg/ml Amphotericin B, at 37° C. and in the presence of 5% $CO_2$. In a first experimental series, these cells were treated with various concentrations (0-400 µM) of OHOD and MOD11 and the number of cells was determined by flow cytometry (FIG. 3A). Both compounds reduced the growth of tumour cells, showing values of $IC_{50}$ (concentration reducing the number of viable cells to 50%) in the range of 50 to 100 µM after 48 hours of incubation. Doses of 200 to 400 µM resulted in total elimination of tumour cells. In a second series, the anti-tumour effectiveness on A549 lung cancer cells was investigated at a single concentration (150 µM) and a time of 48 hours (FIG. 3B). In these cultures, incubation with 150 µM of α-derivatives of cis-monounsaturated fatty acids caused an inhibition of tumour cell growth, indicating that these are effective molecules for cancer treatment. The molecules with derivatives on the α-carbon (independently of the type of modification) and with a double bond in cis configuration, in agreement with the formula indicated above (but not in trans configuration), showed anti-tumour effectiveness. By contrast, molecules lacking a modification on the α-carbon (EE, DE, HD, OD, EO, HDO, ODO) did not show anti-tumour effectiveness. Similarly, molecules with a double bond in trans configuration (tOHOD) or without a double bond (OHS, EO, HDO, ODO, OHS) lacked anti-tumour effectiveness. Obviously, among the previous molecules, some lacked both modifications on the α-carbon and the double bond in cis configuration (EO, HDO, ODO) and had no therapeutic effect. These results demonstrate that only those fatty acids with structures corresponding to Formula I are therapeutically effective.

In a second experimental series, designed to discover whether these molecules are effective in treatment of different types of tumours, the effect of OHOD at various concentrations on human cells of different types of cancer was studied. These experiments were performed as described before, except that the M220 and HT-29 cell lines were cultured in DMEM medium and the MDA-MB-231 line was incubated in Leibowitz L-15 medium supplemented with 15% foetal bovine albumin. It was found that these molecules have a broad spectrum of action, so they can be used for the treatment of various types of cancer (lung, glioma, prostate, breast, pancreas, leukaemia, uterus, colon, etc., Table 2). Given that these molecules did not induce serious secondary effects, can be administered orally and can be taken in large quantities, they can be used as nutraceutical as well as pharmaceutical preparations. Where the nature of the tumour process requires, application can be topical (use on the skin of active products for the treatment of melanoma and other cutaneous abnormalities of cancerous nature), which can be considered as cosmetic treatments when attempts are made to correct aesthetic defects.

TABLE 2

| Cell line | Type of cancer | Mechanism of action[1] | Anti-tumour effect[2] |
|---|---|---|---|
| PC3 | Prostate | P A | +++ |
| LNcaP | Prostate | A | +++ |
| MDA-MB-231 | Breast | A | ++ |
| M220 | Pancreas | A | ++ |
| L-1210 | Lym-Leukaemia | A | +++ |
| Jurkat | Lym-Leukaemia | A | +++ |
| HL-60 | Myel-Leukaemia | P D A | +++ |
| HeLa | Cervix | A | +++ |
| HT-29 | Colon | A | ++ |
| C-6 | Glio-Brain | P D | +++ |
| SH-SY5Y | Neuroblastoma | P | + |
| A549 | Lung | P D | +++ |
| T98G | Glioma | D | +++ |
| A172 | Glioma | D | ++ |
| A118 | Glioma | D | +++ |
| SF-767 | Glioma | D | ++ |
| U87-MG | Glioma | D | +++ |
| SF-268 | Glioma | nd | +++ |
| MCF7 | Breast | nd | +++ |
| NCI-H460 | Lung (CPNM) | nd | +++ |
| IMR90 | Normal Fibroblasts | nd | − |

[1] P [anti-proliferative] D [differentiation] A [apoptosis] nd [not determined]
[2] +[inhibition of growth], ++[total halt of growth], +++[total removal of tumour cells]

Furthermore, α-derivatives of cis-monounsaturated fatty acids are capable of inducing cadherin expression. Cadherin is a cellular adhesion protein. Cells expressing cadherin are often not displaced from their tissue location as they adhere to the surrounding cells. Tumour cells that lose the capacity to synthesise this protein can migrate from the tissue in which they were generated to other body tissues where they can develop a new tumour focus by the process known as metastasis. In treatments with α-derivatives of cis-monounsaturated the fatty acids, a significant increase in cadherin levels was observed (compare FIGS. 4A and 4B). The invasive capacity of cancer cells was also investigated in a culture plate invasion model. In this model, cells are allowed to grow until they invade the whole substrate of the culture dish. Then, an area of the culture dish is scraped and the number of cells invading this region at various times, in the presence and absence of the anti-metastasis compound is counted. As FIGS. 5A and 5B shows, lung cancer cells cultivated in the presence of OHOD had a lower invasive capacity than untreated cells. These results indicate that α-derivatives of cis-monounsaturated fatty acids can be used to prevent or treat the development of tumour metastasis.

In addition, α-derivatives of cis-monounsaturated fatty acids impeded the proliferation of vascular cells (see below), which prevents the formation of blood vessels necessary for tumour development. Therefore, these molecules can be used as tumour anti-angiogenic agents.

Figure 6A:
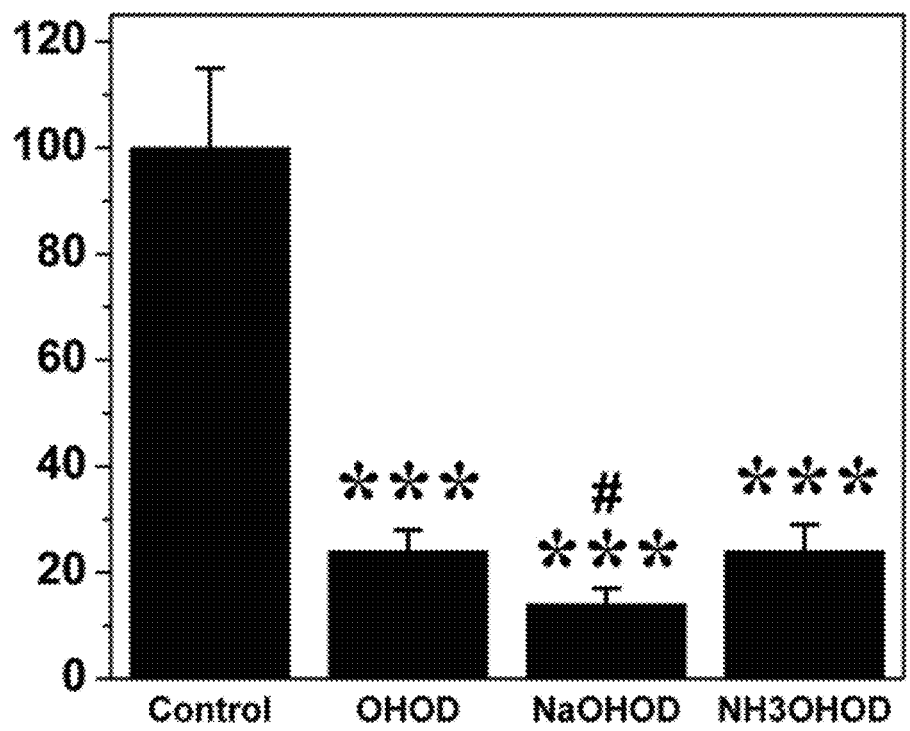
FIG. 6A. Effect of different salts of OHOD on human lung cancer in an animal cancer model. The volume of tumours in nude mice infected with SF767 human brain cancer cells (expressed as a percent compared to control) receiving various treatments. The animals received a vehicle (water: Control), 600 mg/kg of OHOD in the form of free fatty acid (OHOD), 600 mg/kg of sodium salt of OHOD (Na—OHOD) or 600 mg/kg of ammonium salt of OHOD ($NH_3$OHOD) daily for 50 days. All the treatments gave rise to significant reductions in the size of tumours in the treated animals (*** $p<0.001$) and the treatment with Na—OHOD was significantly more potent than the treatment with the free fatty acid, OHOD (# $p<0.05$).
Figure 6B:
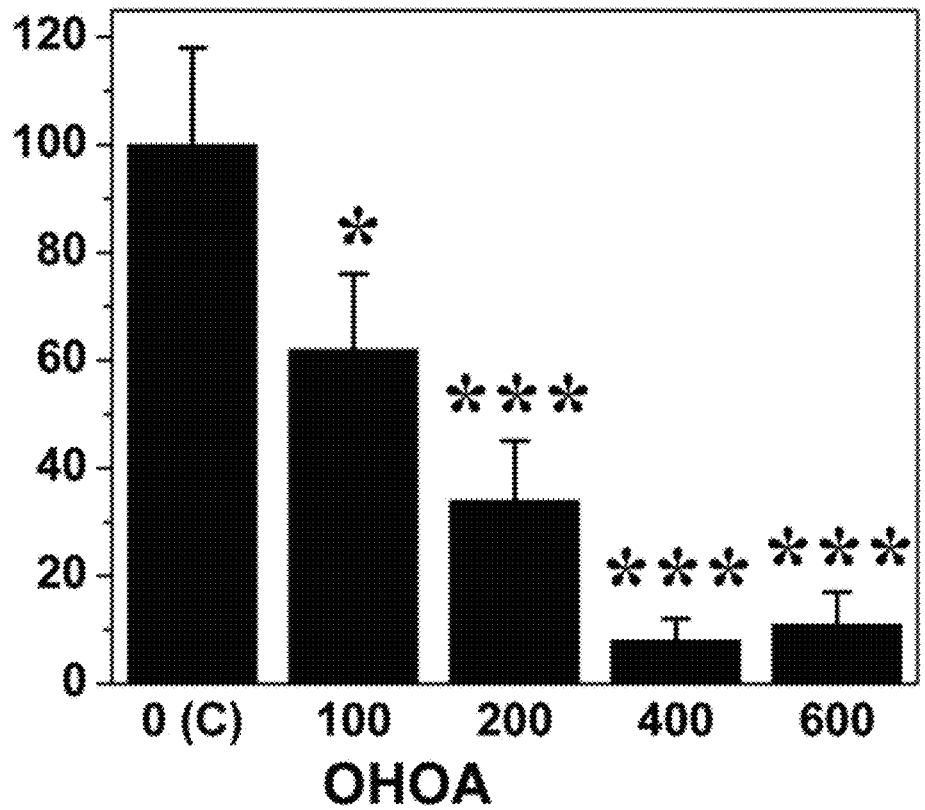
FIG. 6B. Effect of different salts of OHOD on human lung cancer in an animal cancer model. The effect of different doses of sodium salt of OHOD (Na—OHOD) are shown on tumour volumes in mice infected with SF767 cells and treated with vehicle (control, 0 mg/kg), 100 mg/kg (100), 200 mg/kg (200), 400 mg/kg (400) and 600 mg/kg (600) for 50 days. * $p<0.05$; *** $p<0.001$.

One important characteristic of the molecules covered in the present invention is that they can form various types of salts. FIG. 6A and Table 5 show the therapeutic effects of various α-derivatives of cis-monounsaturated fatty acids and their salts. In this sense, perhaps due to better absorption or distribution of these molecules, some of these compounds have significantly higher effects than those shown by the free fatty acid forms, suggesting that such forms would be preferable when preparing a medicine or designing a therapy for the treatment of this disease. The specificity of this effect is determined by the relation between the dose and the effect these molecules have on the volume of human tumours implanted in animals (FIG. 6B).

Figure 7A:
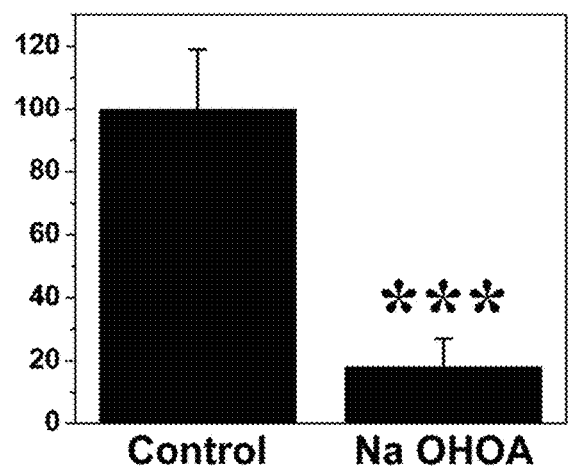
FIG. 7A. Effect of the sodium salt of OHOD (Na—OHOD) on various types of human tumours in animal models. Effect of Na—OHOD (600 mg/kg daily for 50 days) on the volume of tumours in immune-deprived mice ("nude") and immune-deprived mice infected with human leukaemia cells (Jurkat cells).
Figure 7B:
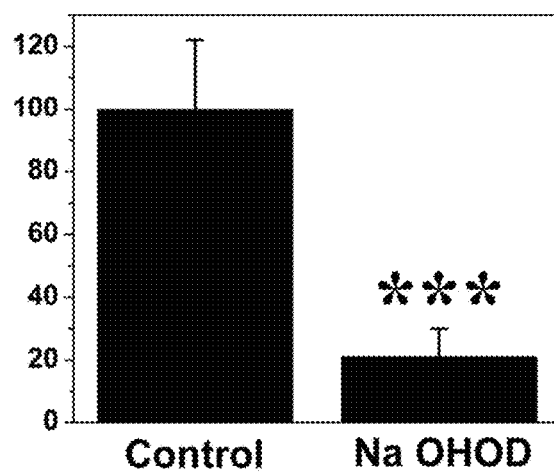
FIG. 7B. Effect of the sodium salt of OHOD (Na—OHOD) on various types of human tumours in animal models. Effect of Na—OHOD (600 mg/kg daily for 50 days) on the volume of tumours in nude mice inoculated with human prostate cancer cells (PC3 cells).
Figure 7C:
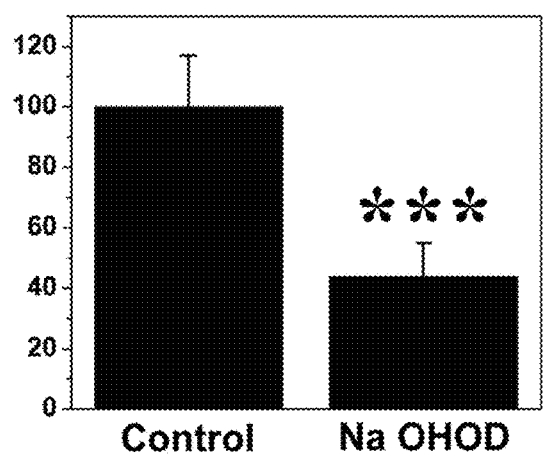
FIG. 7C. Effect of the sodium salt of OHOD (Na—OHOD) on various types of human tumours in animal models. Effect of Na—OHOD (600 mg/kg daily for 50 days) on the volume of tumours in nude mice inoculated with human breast cancer cells (MDA-MB-231 cells).
Figure 7D:
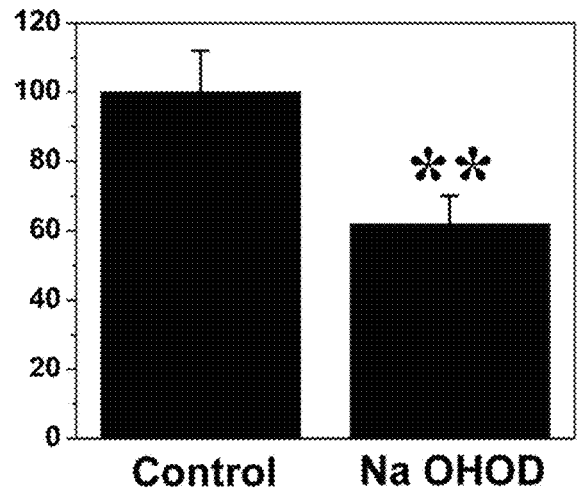
FIG. 7D. Effect of the sodium salt of OHOD (Na—OHOD) on various types of human tumours in animal models. Idem with human colon cancer cells (HT29 cells). All the treatments were continued for 50 days and the control animals were treated with vehicle (water).  $p<0.01$; * $p<0.001$.

Given that the Na—OHOD form (sodium salt of OHOD) is more effective than the corresponding free fatty acid, its anti-tumour action was studied in immune-deprived mice following xenotransplantation of various types of human cancers: leukaemia (FIG. 7A), prostate cancer (FIG. 7B), breast cancer (FIG. 7C) and colon cancer (FIG. 7D).

Figure 8A:
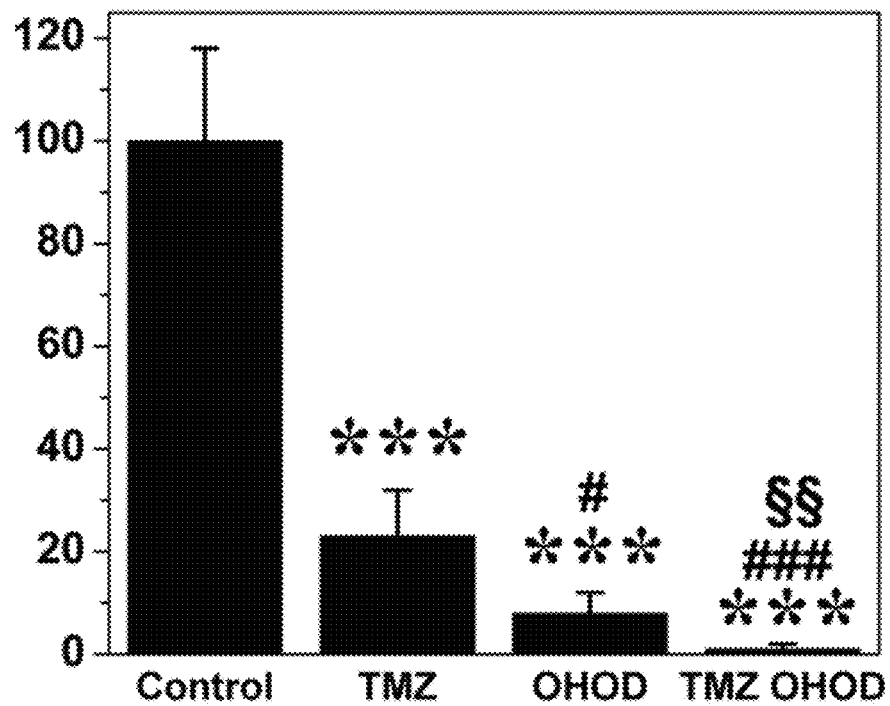
FIG. 8A. Effect of Na—OHOD (sodium salt of OHOD) and combinations with various pharmaceuticals: temozolomide (TMZ), erlotinib, gemcitabine and cisplatin (cis-Pt) on various types of human cancers in models. Effect of treatments with vehicle (Control), temozolomide (TMZ, 80 mg/kg), Na—OHOD (OHOD, 600 mg/kg) and TMZ plus Na—OHOD (simultaneously at the same doses) for 60 days in immune-deprived mice infected with human brain cancer (SF767).
Figure 8B:
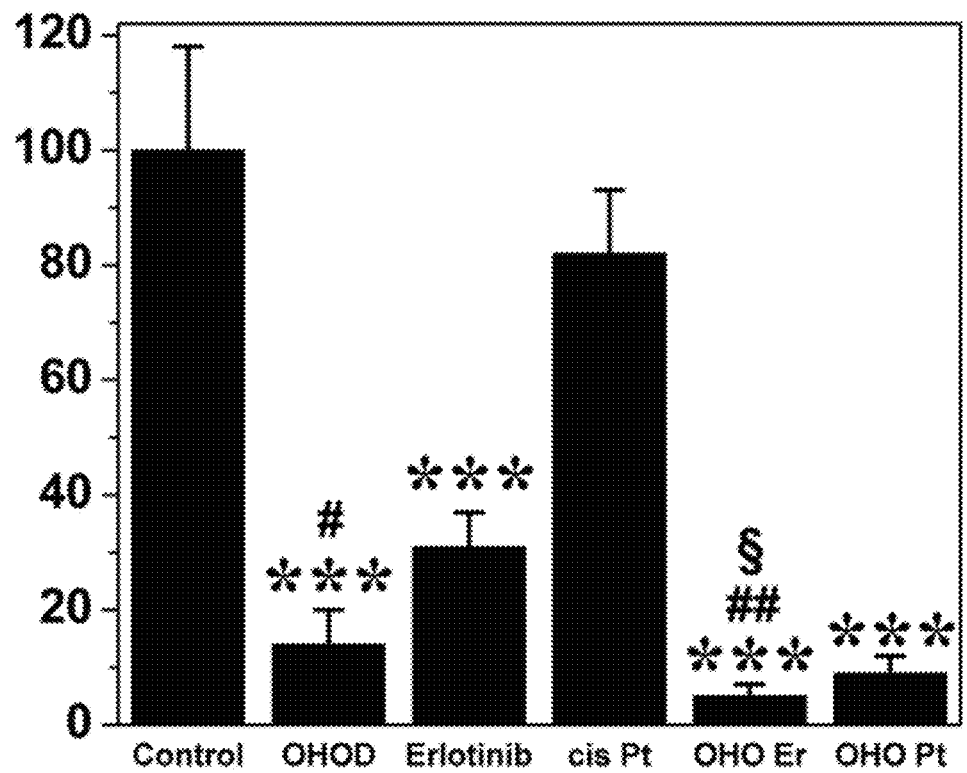
FIG. 8B. Effect of Na—OHOD (sodium salt of OHOD) and combinations with various pharmaceuticals: temozolomide (TMZ), erlotinib, gemcitabine and cisplatin (cis-Pt) on various types of human cancers in models. Idem, with Na—OHOD (OHOD, 600 mg/kg), erlotinib (Erlotinib, 40 mg/kg), cisplatin (cis-Pt, 100 mg/kg), plus erlotinib (OHO Er) or Na—OHOD plus cisplatin (OHO Pt) in nude mice infected with human lung cancer cells (A549).
Figure 8C:
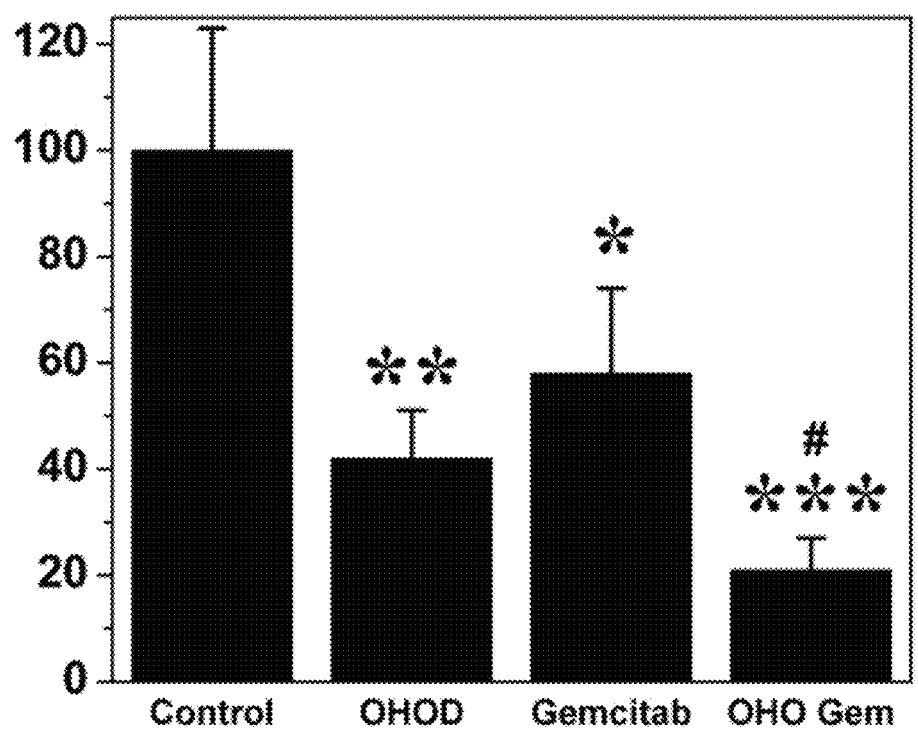
FIG. 8C. Effect of Na—OHOD (sodium salt of OHOD) and combinations with various pharmaceuticals: temozolomide (TMZ), erlotinib, gemcitabine and cisplatin (cis-Pt) on various types of human cancers in models. Idem with Na—OHOD (OHOD, 600 mg/kg), Gemcitabine (Gemcitab, 40 mg/kg) or Na—OHOD plus Gemcitabine (OHO Gem) using the same doses in nude mice infected with human pancreas cancer cells (BXPC3).

Given that the α-derivatives of cis-monounsaturated fatty acids have a very different mechanism of action to that of other anti-tumour pharmaceuticals currently used, the combination of these fatty acids with any anti-tumour pharmaceutical can give rise to higher effectiveness and they can even be successful in treating animals infected with human cancers. FIGS. 8A-8C shows the effect of Na—OHOD alone and in combination with temozolomide, erlotinib, gemcitabine and cisplatin for the treatment of human glioma (brain cancer), human lung cancer and human pancreas cancer in immune-deprived mice models. On the one hand, Na—OHOD was observed to be more effective than the other pharmaceuticals used in humans for cancer treatment. On the other hand, the combination of Na—OHOD with any of these pharmaceuticals gave rise to marked reductions in the volume of tumours and significantly smaller tumours than those after either Na—OHOD given alone or any of the anti-tumour pharmaceuticals indicated above given alone. Furthermore, the residual tumour observed in the majority of animals treated with Na—OHOD and in practically all of those treated with the two molecules simultaneously were made up of dead cells without the capacity to regenerate the tumour. Thus, it can be considered that these combined therapies were effective in treating human tumours implanted into animals.

All this information indicates that α-derivatives of cis-monounsaturated fatty acids can be used in (a) prevention and (b) treatment of cancer by their direct effect on tumour cells. In addition, they are agents with a broad spectrum as they impede the growth of a wide range of tumour cells of very different types. Because they are not toxic they can be used in populations at high risk such as smokers, people exposed to biological or radiological risks that can cause cancer development, carriers of genetic or somatic abnormalities associated with the development of diverse types of tumours, etc. They can also be used in the prevention and treatment of metastasis and angiogenesis processes in patients in which some tumour process may have developed. These molecules can be administered orally and do not show apparent toxic effects, so they can be used as medicines or as functional foods. In addition, their use in skin tumours can be via the topical route.

Example 2

Use of the Fatty Acids of the Invention for the Prevention and/or Treatment of Vascular Cell Proliferation and Other Pathologies of the Heart and Blood Vessels The proliferation of vascular cells lies at the base of certain pathologies such as atherosclerosis, cardiomyopathy, cardiac hyperplasia, hypertension and other cardiac and vascular pathologies as well as tumour angiogenesis. To determine the effectiveness of α-derivatives of cis-monounsaturated fatty acids against the proliferation of vascular cells, the effect of various fatty acids on the multiplication of A10 cells, which are normal vascular cells of originating in the aorta, was studied. The α-derivatives of cis-monounsaturated fatty acids showed a high potency for inhibiting the hyper-proliferation of A10 vascular cells. This effect is not toxic as the number of cells did not reduce after the addition of the compounds, but their proliferation in the presence of foetal serum, which contains molecules that induce cellular multiplication, was prevented. For culture of A10 cells, RPMI 1640 medium supplemented with foetal bovine serum was used, using other additives and conditions previously indicated. The fatty acids listed in Table 1 were added to the culture medium using two growth controls. The first of these lacked any fatty acid, whereas the second lacked fatty acids and foetal bovine serum (without serum). Finally, the cells were counted by flow cytometry.

Figure 9:
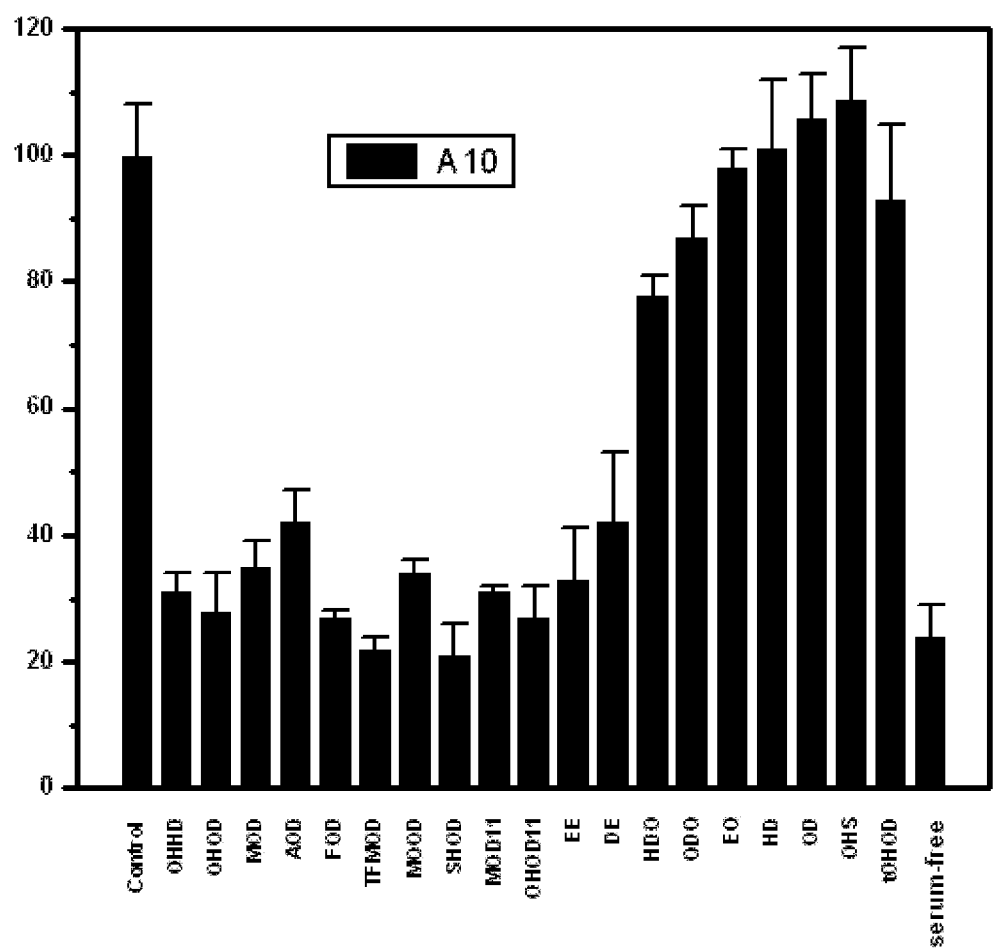
FIG. 9. Effect of various molecules on the proliferation of A10 aorta cells after incubations of 48 hours at a concentration of 200 μM. The fatty acids used are shown on the horizontal axis and the number of cells (% control) are shown on the vertical axis. All the cells grew in identical conditions of temperature, pH and culture medium, except one of the flasks from which the serum was removed (without serum). The fatty acids of the invention induced a halt in cellular proliferation similar to that caused by removal of foetal bovine serum (which contains many cellular growth factors) at a concentration of 200 μM ($p<0.05$ in all cases). This results indicates that these molecules stop the proliferation of cardiovascular cells without having a toxic effect (the number of cells is the same or higher than in the sample without serum).

The α-derivatives of cis-monounsaturated fatty acids at a concentration of 200 μM induced a halt in cellular proliferation similar to that caused by removal of foetal bovine serum (which contains many cellular growth factors) (FIG. 9). These data indicate that α-derivatives of cis-monounsaturated fatty acids are molecules that can be used for the prevention and treatment of atherosclerosis, cardiomyopathy, angiogenesis dependent on tumours, cardiac hyperplasia, hypertension and other related pathologies through medicines or functional foods.

By contrast, fatty acids that do not have double bonds or where the double bond has the trans configuration were not effective in reducing the proliferation of A10 aorta cells. Similarly, fatty acids that did not have modifications on the α-carbon did not have significant effects on the proliferation of A10 cells. By contrast, fatty acids with the double bond in the cis configuration and a modification on the α-carbon produced an effect, independently of the radical that was introduced on this carbon. Tumour angiogenesis is mediated by the proliferation of vascular cells around the cancerous cells. Therefore, α-derivatives of cis-monounsaturated fatty acids are potent anti-angiogenic factors that can be used to prevent the proliferation of blood vessels providing nutrients to newly formed tumours.

Figure 10:
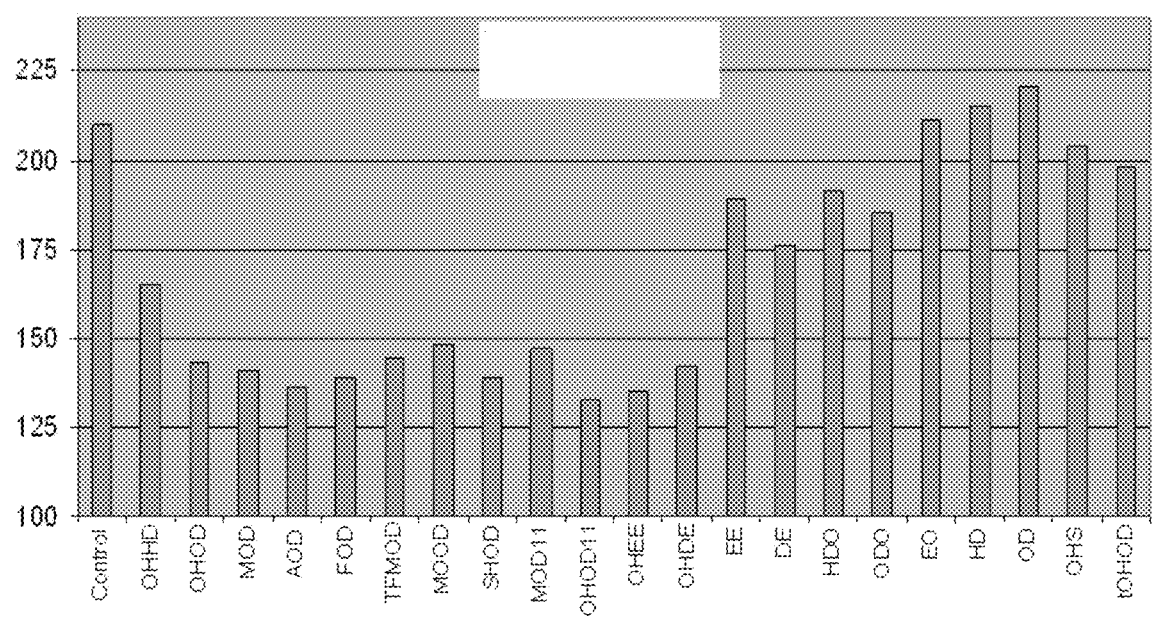
FIG. 10. Effect of various fatty acids in the prevention and treatment of hypertension development in SHR rats. The fatty acids used are shown on the horizontal axis and the arterial pressure (Hg) is shown on the vertical axis. Animals treated with the fatty acids of the invention were observed not to have developed hypertension ($p<0.05$ in all cases), whereas untreated animals or animals treated with fatty acids not having the structure shown in Formula I developed hypertension.

In another series of experiments, the effectiveness of various fatty acids in preventing the appearance of hypertension was investigated. Hypertensive rats (SHR) were treated with α-derivatives of cis-monounsaturated fatty acids and other fatty acids (FIG. 10). SHR rats are normotensive during the first months of life until they reach maturity and acquire a hypertensive condition (between 3 and 4 months of age). In order to determine whether the derivatives used were capable of preventing the development of hypertension, 10-week old SHR rats were treated with various fatty acids. The animals are still normotensive at this age, having an arterial pressure of between 130 and 140 mmHg, which was measured at the start of the treatment. The animals were divided into experimental groups of 8 animals in such a way that the average arterial pressure was similar in all the groups (average values between 128 and 132 mmHg for all the groups at the start of the experiment). The study of the prevention of hypertension development was performed by administering a dose of 200 mg/kg per day to the animals for 10 weeks and measuring their arterial pressure at the end of the treatment. In FIG. 10, animals treated with α-derivatives of cis-monounsaturated fatty acids were observed not to have developed hypertension, whereas untreated animals or animals treated with fatty acids not having the structure shown in Formula I developed hypertension. This result is clearly different from the effect of hypertension treatment because prevention stops animals from suffering hypertension at some time in their lives. Therefore, prevention of hypertension development avoids all the problems associated with this state such as cardiac hypertrophy, cardiovascular accident risk, isquemia, etc. In fact, in animals treated with α-derivatives of cis-monounsaturated fatty acids significant reductions in the weight of the heart compared to hypertensive animals (reductions of between 2% and 7% in weight of the heart of SHR rats for the compounds covered in the present invention) were observed. Hypertensive animals perform an excess cardiac effort to compensate for the resistance of the vascular system to the passage of blood, so they present cardiac hypertrophy. Therefore the compounds of the present invention can be used for the treatment of various pathologies related to the processes of cardiac hypertrophy.

In another experiment, a series of cis-monounsaturated fatty acids were used (Table 5), again showing that Na—OHOD was more effective than OHOD, indicating that the substitution of the hydrogen (H) in the R position by sodium (Na) increases the therapeutic power of the fatty acid in hypertension treatment.

All these results demonstrate that the structure indicated in Formula I is the most appropriate both for the prevention and for the treatment of pathologies related to cellular proliferation of the heart and blood vessels. These treatments can be administered as pharmaceuticals, nutraceuticals or topical/aesthetic preparations.

Figure 11:
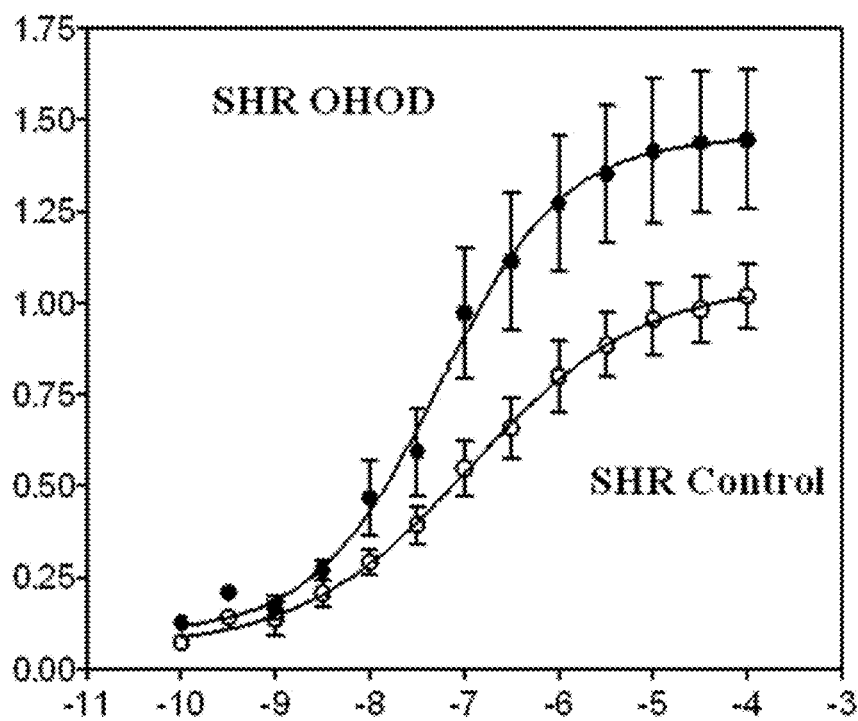
FIG. 11. Effect of OHOD on the contractile response induced by noradrenalin (NA) in aortas of SHR rats. The logarithm of NA is shown on the horizontal axis and the concentration (g) is shown on the vertical axis. The aortas were treated with OHOD (filled circles) or vehicle (empty circles) for 60 minutes in an organ bath at 37° C. in Ringer medium with oxygen. The figure shows that the contractile response induced by noradrenalin (NA) was much higher in rat aortas pre-treated with this fatty acid ($p<0.05$). This result clearly indicates that the flexibility of the vascular tissue increases significantly ($p<0.05$) in the presence of the fatty acids of the invention.

Atherosclerosis or arteriosclerosis is a pathology characterised by the loss of contractility of blood vessels. This loss is associated with diverse factors, among which is the formation of deposits on the vascular lumen giving rise to the proliferation of vascular cells, reduction of blood flow and vasoconstrictor and vasodilator responses to neurotransmitters (such as noradrenalin) and to hormones. In studies in isolated rat aorta in organ bath, it was shown that the contraction power of the aortic muscle in response to noradrenalin increased very markedly after pre-treatments with OHOD acid. In addition, all the compounds with the structure of Formula I had similar effects on vascular muscle. These results clearly indicate the capacity of these compounds in preventing or treating atherosclerosis and related pathologies. FIG. 11 shows the effect of in vitro pre-treatment (organ bath) with OHOD on the contraction capacity of SHR rat aortas. The figure shows that the contraction capacity induced by noradrenalin (NA) was much higher in the aortas of rats pre-treated with this fatty acid. This result clearly indicates that the vascular tissue flexibility increased significantly ($p<0.05$) in the presence of this compound, demonstrating the utility of α-derivatives of cis-monounsaturated fatty acids in the prevention and treatment of atherosclerosis and other cardiovascular pathologies. In addition, the improvement of the aorta contractile response indicates that these compounds can also be used for the maintenance of vascular tissue in healthy subjects and in the treatment of damaged vessels in patients with cardiovascular pathologies.

Example 3

Figure 12:
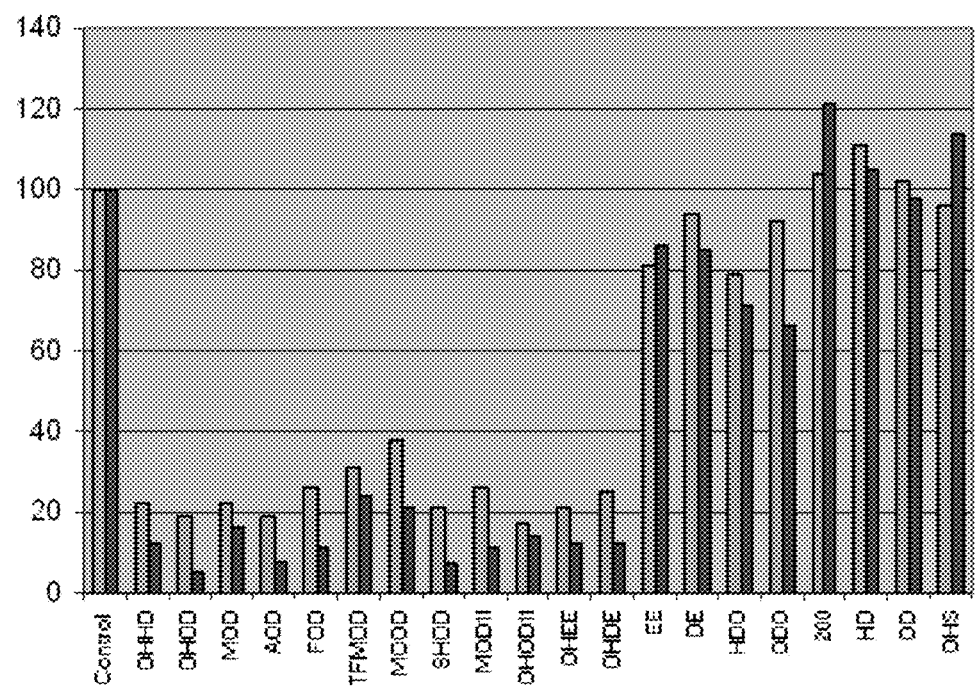
FIG. 12. Effect of the fatty acids of the invention (shown on the horizontal axis) on the production of melanin in mice melanocytes (B16 cells, lighter left bar) and on the proliferation of adipocytes (3T3-L1 cells, darker right bar). The results are the average of three independent experiments. In this sense, concentrations of 100 μM of these compounds for 48 hours caused reductions in the melanin content of B16 cells (p<0.05 in all cases). Also the molecules that have the structure of Formula I inhibited the growth of 3T3-L1 cells (adipose cells or adipocytes, p<0.05 in all cases), whereas the molecules that do not have the structure of Formula I did not have significant effects on the proliferation of adipocytes.

Use of the Fatty Acids of the Invention for the Prevention and/or Treatment of Cutaneous Pathologies and Related Diseases Abnormalities in the production of melanin give rise to abnormalities in cutaneous pigmentation and can be pathological in nature. To study the potential application of α-derivatives of cis-monounsaturated fatty acids in the treatment of melanopathies, the production of melanin in mice melanocytes (B16 cells) was measured. Cells were broken with NaOH and the concentration of melanin was determined by absorption spectroscopy at 490 nm, using the method previously described by Curto et al. (1999). Concentrations of 100 μM of these compounds for 48 hours caused reductions in the melanin content of B16 cells (FIG. 12). These results indicate that the α-derivatives of cis-monounsaturated fatty acids with the structure of Formula I can be used for the treatment of dermatological problems related to pigmentation pathologies. Similarly to the findings with treatments of other pathologies, fatty acids that do not have the structure of Formula I lacked significant effects in regulating melanin content (FIG. 12).

FIG. 12 also shows the effect of α-derivatives of cis-monounsaturated fatty acids (100 μM, 48 hours) on the proliferation of adipocytes (3T3-L1 cells). The molecules that have the structure of Formula I inhibited the growth of 3T3-L1 cells, whereas molecules that do not have the structure of Formula I did not have significant effects on the proliferation of adipocytes (FIG. 12). These types of adipose cells can grow anomalously or multiply anomalously in subcutaneous areas (hypertrophy or hyperplasia of the adipocytes). The abnormal growth can give rise to pathological processes of various types such as obesity and cellulitis.

The results shown here indicate that the α-derivatives of cis-monounsaturated fatty acids can be used for the prevention and treatment of pathologies such as obesity, cellulitis, psoriasis, skin stains and similar. Given the special typology of skin and the layers beneath it, the treatment of some of these pathologies can be performed topically, so these molecules can be used as cosmetics. These pathologies can also be treated through pharmacological and nutraceutical preparations.

Example 4

Use of the Fatty Acids of the Invention for the Prevention and/or Treatment of Metabolopathies (Metabolic Pathologies: Hypercholesterolemia, Hypertriglyceridemia, Diabetes) and Obesity Metabolic diseases form a set of pathologies characterised by the accumulation or deficit of certain molecules (cholesterol, triglycerides, glucose, etc.) in the serum or tissues. These changes are the reflection of dysfunctions that are normally associated with errors in the activity of certain enzymes or in the control of these proteins. Among the most important metabolopathies are hypercholesterolemia (elevated levels of cholesterol), hypertriglyceridemia (elevated levels of triglycerides) and diabetes (elevated levels of glucose). These pathologies have high rates of incidence, morbidity and mortality, so that treatment is a first order necessity. In this sense, treatment with OHOD resulted in significant reduction in the levels of cholesterol, triglycerides and glucose (FIG. 13) in Sprague-Dawley rats (females of 300 g). For these experiments, the dose of fatty acid indicated (0, 200, 400 and 600 mg/kg) was supplied daily via the oral route. At the end of the treatment (30 days), blood was sampled from control and treated animals (n=6) and the levels of cholesterol, triglycerides and glucose were determined using standard colorimetric methods. The effects observed depended on the dose, indicating that the effect was specific.

Figure 13:
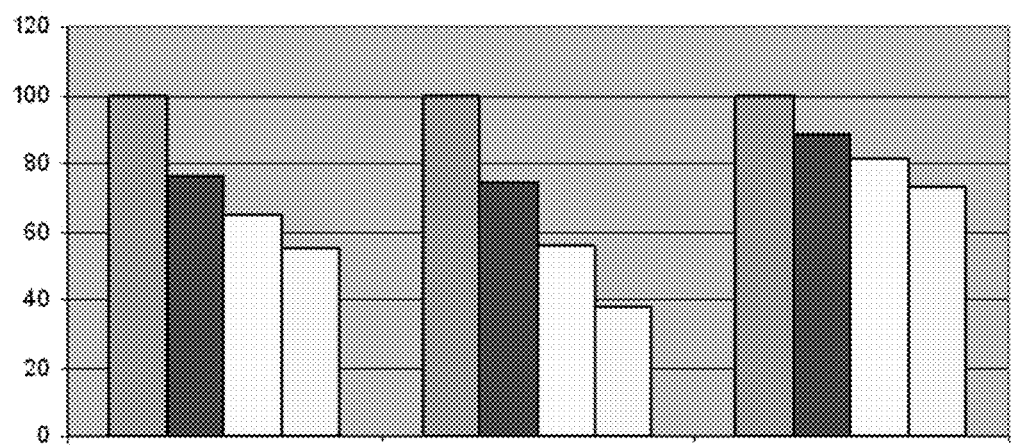
FIG. 13. The four bars, from left to right respectively, show the effect of treatments with vehicle (control, first bar), OHOD at 200 mg/kg (second bar), OHOD at 400 mg/kg (third bar) and OHOD at 600 mg/kg (fourth bar) on the cholesterol levels (group of four bars to the left), triglycerides (group of four bars in the middle) and glucose (group of four bars to the right). The treatments were oral in all cases and were maintained for 30 days. The values indicated are the average obtained in 6 animals per group. Treatment with OHOD was observed to have caused significant reductions in the levels of cholesterol, triglycerides and glucose (p<0.05 in all cases).
Figure 14:
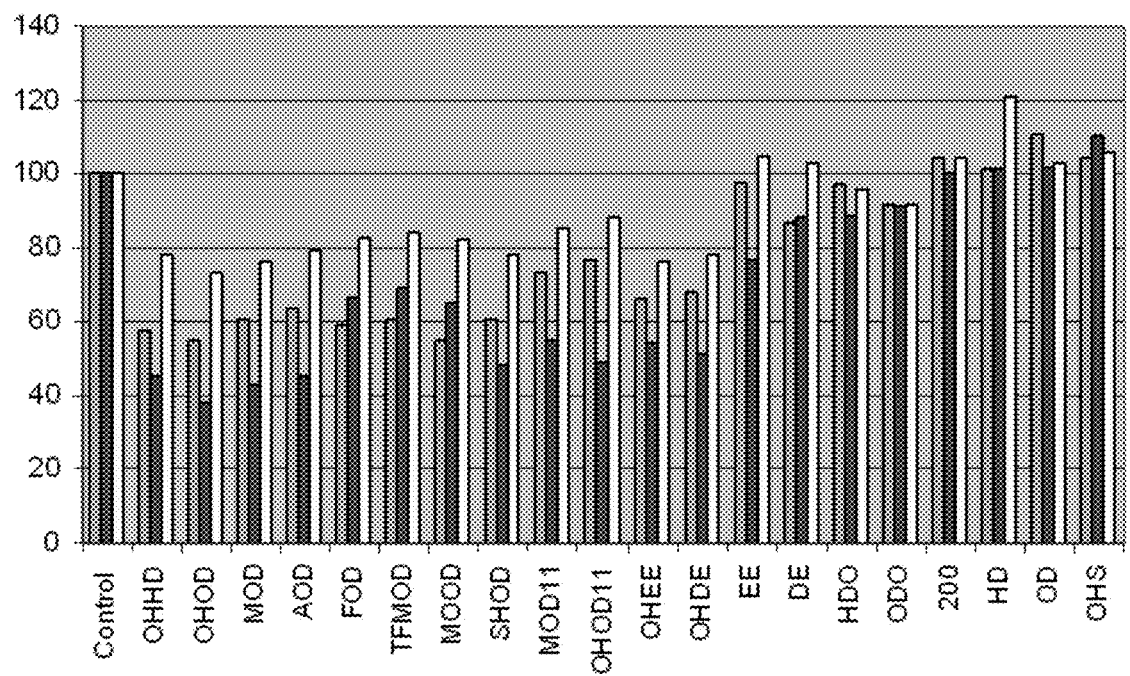
FIG. 14. Effect of treatment with vehicle (control) or with the fatty acids of the invention (600 mg/kg) on the levels of cholesterol, triglycerides and glucose. The values indicated are the average of the values obtained in 6 animals. Each group of three bars represents treatment with a different fatty acid with the left bar corresponding to cholesterol, the middle bar to triglycerides and the right bar to glucose. The fatty acids with the structure of Formula I were observed to cause significant reductions in the three parameters (p<0.05), whereas analogous molecules that do not have the structure of Formula I did not have effects for effective treatment of metabolic pathologies such as hypercholesterolemia, hypertriglyceridemia, diabetes and metabolic syndrome.

In a further experiment, the effect of various molecules at a single dose (600 mg/kg) was investigated. In these studies, the α-derivatives of cis-monounsaturated fatty acids showed a significant effect on the reduction of cholesterol, triglycerides and glucose. By contrast, molecules that did not have the structure indicated in Formula I did not exhibit therapeutic effects (FIG. 13). In this sense, modification on the α-carbon and the double bond in cis configuration are crucial elements for producing the therapeutic effect indicated above. Analogous molecules that did not have the structure of Formula I were not effective as treatments for hypercholesterolemia, hypertriglyceridemia and diabetes (FIG. 14). Finally, the effect of α-derivatives of cis-monounsaturated fatty acids on the prevention of obesity was investigated. For this, a model of rat obesity induced by a cafeteria diet, where the hypercaloric food increases the weight of the animals very markedly, was used. There were various experimental groups (see Table 3), each of which consisted of 6 female Wistar Kyoto rats of 250-300 g in weight. All the animals received a standard diet for 2 weeks. In addition, 2 of the groups received an oral preventative pre-treatment of vehicle and the other groups received 300 mg/kg of the fatty acids indicated below. Afterwards, one of the control groups was maintained on a standard diet (lean control) and the other was fed on a cafeteria diet (obese control). The treated animal groups were fed on the cafeteria diet. Preventative pre-treatment was maintained for all the groups. After two weeks on these diets, the lean control group had increased their body weight by an average of 16±16 g, while the obese control group had increased their body weight by an average of 43±17 g (statistically significance difference, p<0.01). Rats treated with α-derivatives of cis-monounsaturated fatty acids showed increases in weight similar to that of the thin control group and significantly less than that of the obese control group (p<0.05) consuming the same diet. Therefore, animals pre-treated with these fatty acids showed marked and statistically significant less weight gain compared to animals receiving an identical cafeteria diet. In this context, the use of certain derivatives (salts) of the fatty acids covered in this invention resulted in a higher therapeutic effect in some cases, with reductions in the levels of cholesterol (CHO) and triglycerides (TG) that were greater than those observed after treatments with the free fatty acids (Table 5).

The weight of treated animals was statistically less than the weight of obese control rats and statistically indistinguishable from that of lean control rats. These results, together with the prevention of weigh gain (Table 3) and the inhibition of adipocyte development (FIG. 12), indicate that α-derivatives of cis-monounsaturated fatty acids are active molecules for the treatment and prevention of the development of obesity. It should be highlighted that in this experimental series with animals (Table 5) there was no pre-treatment, which indicates that Na—OHOD was more effective for the treatment of obesity than OHOD. Also, both the salts and other pharmaceutically acceptable forms for the treatment of these and other metabolopathies showed high therapeutic activity so that any of them may be used or chosen from among those forms showing the best pharmacological safety.

TABLE 3

| DIET RECEIVED AND PREVENTATIVE TREATMENT | Starting weight | Final weight |
|---|---|---|
| Standard + vehicle treatment (lean control) | 264 ± 21 | 280 ± 16 |
| Cafeteria + vehicle treatment (obese control) | 265 ± 14 | 308 ± 17 |
| Cafeteria + OHHD treatment | 259 ± 21 | 275 ± 19* |
| Cafeteria + OHOD treatment | 269 ± 11 | 284 ± 13* |
| Cafeteria + MOD treatment | 255 ± 12 | 268 ± 12* |
| Cafeteria + AOD treatment | 249 ± 14 | 272 ± 15* |
| Cafeteria + FOD treatment | 261 ± 13 | 279 ± 13* |
| Cafeteria + TFMOD treatment | 262 ± 12 | 278 ± 14* |
| Cafeteria + MOOD treatment | 251 ± 21 | 263 ± 22* |
| Cafeteria + SHOD treatment | 254 ± 16 | 269 ± 16* |
| Cafeteria + MOD11 treatment | 257 ± 16 | 274 ± 18* |
| Cafeteria + OHOD11 treatment | 256 ± 10 | 269 ± 12* |
| Cafeteria + OHEE treatment | 252 ± 9 | 264 ± 11* |
| Cafeteria + OHDE treatment | 260 ± 12 | 273 ± 15* |
| Cafeteria + EE treatment | 258 ± 14 | 301 ± 17‡ |
| Cafeteria + DE treatment | 253 ± 11 | 305 ± 12‡ |
| Cafeteria + HDO treatment | 255 ± 15 | 299 ± 15‡ |
| Cafeteria + ODO treatment | 259 ± 19 | 301 ± 18‡ |
| Cafeteria + EO treatment | 262 ± 12 | 298 ± 12‡ |
| Cafeteria + HD treatment | 260 ± 16 | 309 ± 15‡ |
| Cafeteria + OD treatment | 259 ± 14 | 311 ± 17‡ |
| Cafeteria + OHS treatment | 251 ± 10 | 314 ± 11‡ |
| Cafeteria + tOHOD treatment | 258 ± 17 | 312 ± 19‡ |

*Significantly lower than obese controls (p < 0.05)
‡Statistically indistinguishable from obese control (p < 0.05)

The combination of various of these pathologies gives rise to a process called metabolic syndrome. The results shown in this section clearly indicate that α-derivatives of cis-monounsaturated fatty acids are very active molecules for the prevention and treatment of hypercholesterolemia, hypertriglyceridemia, diabetes, metabolic syndrome, obesity and other metabolopathies through pharmaceutical or nutraceutical preparations.

Example 5

Use of the Fatty Acids of the Invention for the Prevention and/or Treatment of Neurodegenerative Pathologies Neurodegenerative processes give rise to a series of diseases with various manifestations, but the common characteristic is degeneration of the cells of the central and/or peripheral nervous system. Some of these neurodegenerative processes such as Alzheimer's disease or senile dementia imply a significant decline in patients' cognitive capacity. Others give rise to motor changes such as Parkinson's disease and various types of sclerosis. Finally, certain neurodegenerative pathologies can result in processes causing blindness, hearing problems, disorientation, changes in affect, etc.

An example of a well characterised neurodegenerative disorder is Alzheimer's disease in which the formation of senile plaques has been observed, formed by the remains of membrane proteins (e.g. the β-amyloid peptide) that are erroneously processed and which accumulate outside the cells and neurofilament tangles that appear inside the cells. This process has been associated with changes in cholesterol metabolism and the consequent alteration of cholesterol levels in the membranes (Raid et al., 2007). In fact, the development of this disease is related to other pathologies in which changes in lipid metabolism, and more specifically in cholesterol, have been described such as those of cardiovascular type.

Sclerosis and other neurodegenerative processes are related to "demyelination", the net result of which is the loss of lipids in the neuronal axon sheath, with consequent changes in the process of propagation of electrical signals. Myelin is a lipid layer that surrounds axons of many neurones and is formed by a succession of spiral folds of the plasma membrane of glial cells (Schwann cells). For these reasons, it is clear that lipids play a very important role in the development of neurodegenerative pathologies.

Figure 15:
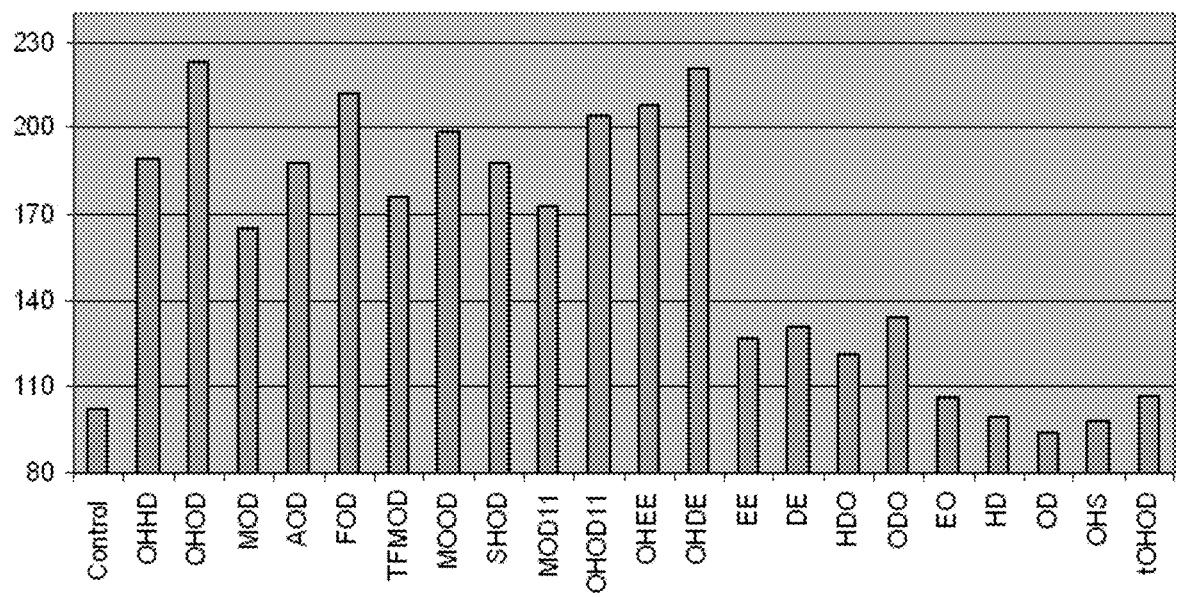
FIG. 15. Cognitive index in mice with Alzheimer's. For this study, six month old mice were used with a series of mutations identical to those causing Alzheimer's disease in humans and which exhibited neurological and cognitive symptoms of this disease (Jackson Laboratories-Charles River). The bars correspond to cognitive index values, determined as the average of the results obtained in the Miller radial arm maze test. In the Miller test the time for finding the platform before learning divided by the time for finding the platform after learning was measured and expressed as 100%. In this test, the time taken by animals treated with vehicle (water, control) was considered to be 100%. Higher values for this parameter correspond to less time to find the platform after learning, caused by an improvement in memory of the animals. In the radial arm maze, the average number of attempts until finding the platform in the maze with stimulus (food) before training divided by the number of attempts after training was taken. This average coefficient in control animals was considered as 100% and an increase in this parameter is due to a smaller number of attempts, in relation to the memory capacity of the animal. The fatty acids used are shown on the horizontal axis. Each group of animals (n=8) were treated with vehicle (control) or the fatty acids of the invention (100 mg/kg). After the study it was observed that the fatty acids of the invention were highly effective at preventing the development of the neurodegenerative process (Alzheimer's) based on the improvement in cognitive parameters (p<0.05 in all cases).

Given that the lipids with the structure of Formula I are capable of reducing cholesterol levels (FIGS. 13 and 14), it is a priori likely that they could be effective for the treatment of neurodegenerative diseases. The α-derivatives of cis-monounsaturated fatty acids were shown in a study to be highly effective in preventing neurodegeneration in an animal model (FIG. 15). The transgenic mice used in this study, which over-express ApoB-100, are characterised by an early start of a syndrome similar to Alzheimer's disease, with similar significant cognitive loss and cyto-histological features to those found in neurodegenerative processes in humans. In these animals, treatments with α-derivatives of cis-monounsaturated fatty acids gave rise to marked and significant improvements of cognitive parameters in animals. For this study, mice (n=8) were treated for 6 months with 100 mg/kg fatty acid administered orally 5 times a week (Monday to Friday). The control group consisted of mice (n=8) treated with vehicle (water) in a similar way to the test group. To determine the cognitive capacity of the animals, a radial maze and the Miller test were used and the cognitive capacity of control animals (untreated) was defined as 100% (Wise et al., 2007; Patil et al., 2006). The cognitive capacity of animals treated with various types of fatty acids was expressed as percentage improvement measured in performing these tests. The results indicated that α-derivatives of cis-monounsaturated fatty acids can be used for the treatment of neurodegenerative pathologies such as Alzheimer's, various types of sclerosis, Parkinson's disease, etc., through pharmaceutical and nutraceutical preparations.

Example 6

Use of the Fatty Acids of the Invention for the Prevention and/or Treatment of Nerve Fibre Lesions and Pain The central nervous system, after the adipose tissue, contains the highest amount of lipids in the organism. From this it can be deduced that lipids will be very important for neurones and glial cells. In this context, the fatty acids covered in the present invention can prevent and treat functional symptoms such as, for example, loss of motor function, neuropathic pain or spasticity induced by a nerve fibre lesion. To prolong the release of OHOD and similar fatty acids after a single injection of the compound, they were bound to bovine serum albumin (albumin-fatty acid complexes or A-AG, where AG can be OHOD) and the recovery of motor activity was observed (FIG. 16).

Figure 16A:
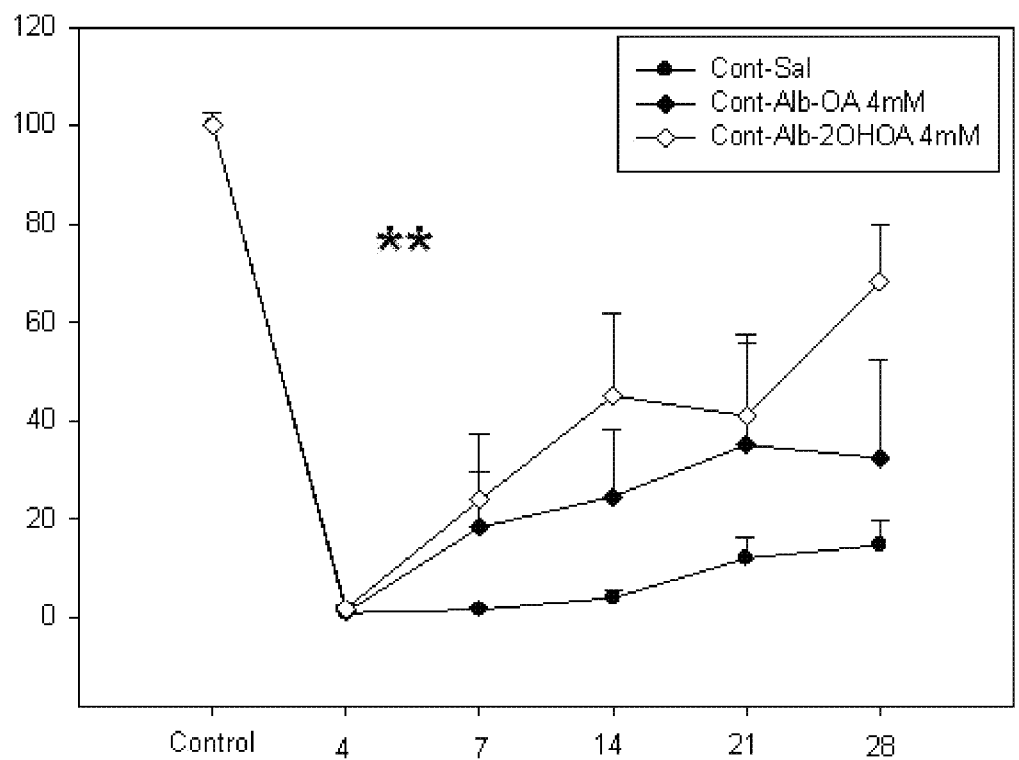
FIG. 16A. Change in motor recovery from 4 to 28 days after nerve fibre lesion (X axis) as a function of voluntary movement on the Rotarod (Y axis) after nerve fibre lesion by contusion (Cont), expressed as the percentage of time spent on the apparatus compared to the control of each group obtained before the contusion (100%). The results for groups treated with 10 µl of saline alone (Sal), Albumin-Oleic acid (Alb-OA 4 mM), Albumin-OHOD (Alb-2OHOD 4 mM) are shown.
Figure 16B:
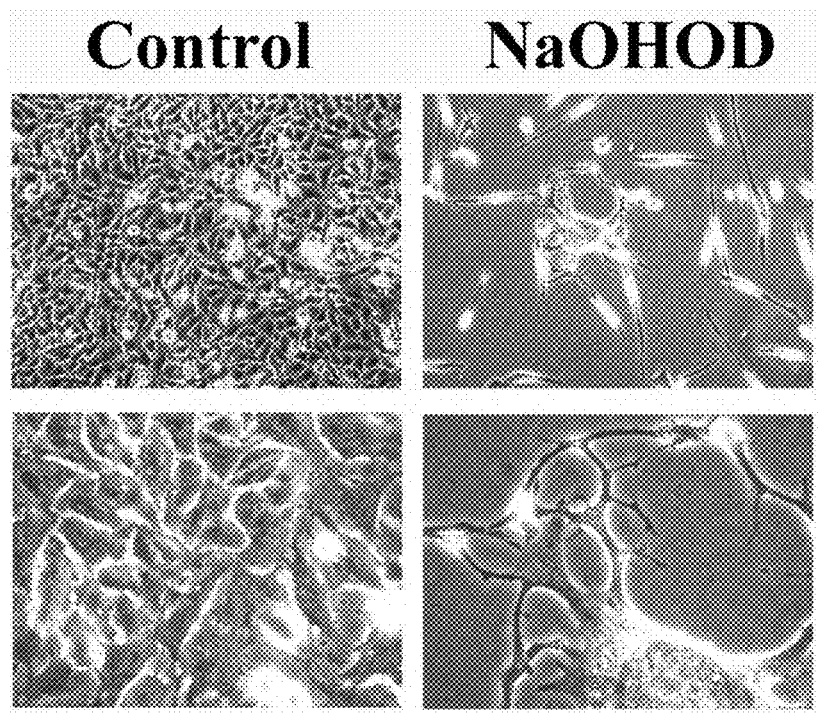
FIG. 16B. Human glioma cells (U118) are astrocytes of the central nervous system (CMS) that have lost their differentiation (Control). In the presence of Na—OHOD (200 µM), glioma cells differentiate and develop towards the glial phenotype, emitting projections typical of astrocytes. This differentiating activity can be involved in neuroregenerative processes necessary for recovery of motor activity. These results show that OHOD and derivatives (e.g. Na—OHOD) were effective in neuroregenerative treatment necessary to treat nerve fibre lesions.

As FIG. 16A shows, albumin-OHOD complex at a dose of 4 mM in 10 μl given by the intrathecal route generally enhanced recovery of voluntary motor function from 4 to 28 days after nerve fibre lesion in rats compared to animals treated with saline or albumin-oleic acid complex. These results demonstrate that albumin-OHOD complex was effective in neuroregeneration and neurotrophy during the chronic phase of nerve fibre lesion. This effect may be due to the induction of neural projection sprouting necessary to re-establish connections lost by the nerve fibre lesion. The effect of OHOD (sodium salt) on the differentiation and emission of projections in U118 cells is shown in FIG. 16B, which demonstrates the neuroregeneration and neurotrophy capacity of the α-derivatives of cis-monounsaturated fatty acids.

Figure 17:
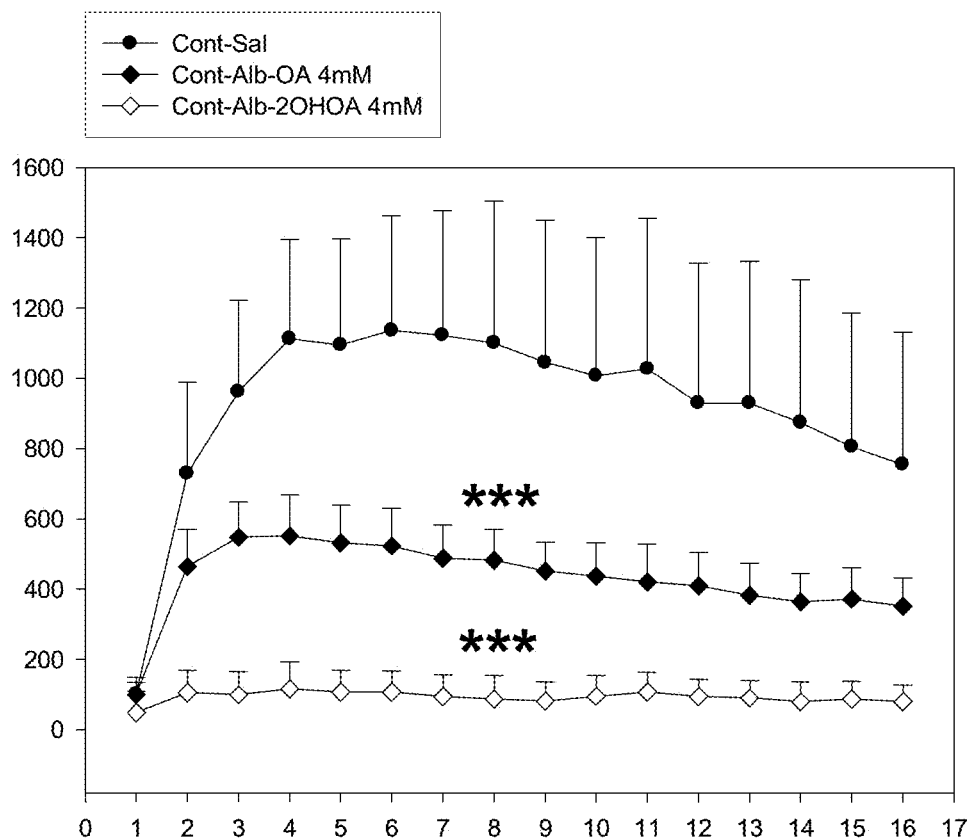
FIG. 17. Effect of 10 µl of sodium saline, Albumin-Oleic acid (Alb-OA-4 mM) and Albumin-2-Hydroxy-Oleic Acid (Alb-2OHOA-4 mM) on the temporal summation of the tibialis anterior plantar reflex (TA) present below a moderate level T8 contusion expressed as a percentage of the initial response. The X-axis of the graph represents the number of stimuli and the Y-axis represents the increase in the integral of the tibialis anterior reflex (as % of the initial response).

In vivo assays have also demonstrated that the administration of a A-AG complex can inhibit changes in the sensitivity and sensorimotor function, so it may have application in the treatment of changes in nociperception and pain. Specifically, rats treated with albumin-OHOD (4 mM, 10 μl by intrathecal route) showed a greater inhibition of the temporal summation of the plantar withdrawal reflex of the tibialis anterior 28 days after nerve fibre lesion compared to rats treated with saline or with albumin-oleic acid (FIG. 17). These results suggest that albumin-OHOD complexes may be highly effective in the treatment of chronic pain.

Therefore the trials performed indicate that the molecules included in the present invention can be used for the prevention of the appearance of motor paralysis and in the treatment of neuropathic pain and spasticity derived from nerve fibre lesions.

In view of the findings above, medicines based on a A-AG complex may enable treatment of nerve fibre lesions, especially of traumatic lesions.

In a particular embodiment, the albumin is selected from native or recombinant albumin of human, bovine, murine and rabbit origin or ovalbumin and lactoalbumin, more preferably the albumin used is human serum albumin or bovine serum albumin, such as was used in the examples of this document. All these albumins have similar structures and functions. For example, a comparison of a sequence of bovine albumin and human albumin showed a correspondence in the amino acid sequence of 76%. The correspondence rises to 88% when conservative changes are taken into account.

For these trials, the albumin-fatty acid complex (A-AG) was prepared in a solution of 2% (w/v) albumin and oleic acid or OHOD was added to a final concentration of 78 mM. A solution of 50% albumin-fatty acid (1:1) was prepared, a concentration of 78 mM, dissolved in saline.

This effect on motor recovery after nerve fibre lesion could be explained by a neurotrophic effect on the lipid membrane of undamaged neurones (e.g. Kim et al., J. Gen Physiol. 2000; 115(3): 287-304), specifically at the base of the neurites, resulting in dentritic growth, high regulation of GAP-43 and the protein associated with microtubules (MAP-2, Tabernero, Lavado et al., 2001; Rodríguez-Rodríguez et al., 2004). The albumin receptor, megalin, has been identified in the membrane of the oligodendrocytes, specifically in the spinal medulla (Wicher et al., J. Neurol. Res. 2006; 83(5):864-73).

The effect on central sensitivity to nocive stimuli after nerve fibre lesion can be explained by regulation of astrogliosis through the lipid membrane by inhibition of the gap junctions by oleic acid (Lavado et al., J. Neurochem. 1997; 69(2):71-8) or by a reduction in the reactive morphology of astrocyte cells by albumin (Manning and Sntheimer, Glia 1997; 20(2):163-72).

Example 7

Use of the Fatty Acids of the Invention for the Prevention and/or Treatment of Inflammatory Processes Tissue and cellular inflammatory processes are characterised by the action of proinflammatory cytokines (interleukin-4, -6, -8, -10, TNF-α, etc.) released by cells of the immune system (lymphocytes, neutrophils, monocytes, macrophages, etc.) after stimulation caused by a pathogen (infection) or antigenic aggression. Inflammatory processes cause a wide variety of diseases, among which are cardiovascular, systemic, locomotor apparatus, ageing and respiratory diseases such as asthma, chronic obstructive pulmonary disease (COPD) and various types of inflammations. This uncontrolled release of proinflammatory cytokines is fundamentally due to pathological activation of NFκB transcription factor (Barnes et al., 1997).

In a cellular inflammation model (U937 monocytes in culture stimulated with bacterial lipopolysaccharide, LPS), α-derivatives of cis-monounsaturated fatty acids (250 µM, 72 h) significantly inhibited the expression of the most important proinflammatory cytokines (IL-6 and TNF-α). By contrast, compounds that did not have the structure of Formula I did not inhibit the expression of these proinflammatory cytokines (FIG. 18).

In an additional study on the release of various proinflammatory cytokines (IL-1b, IL-6, IL-8, IL-10) and TNF-α in U937 monocytes stimulated with bacterial lipopolysaccharide (LPS), a marked reduction in the levels of these molecules was observed after treatments with OHHD at a concentration of 250 µM and 72 h incubation (Table 4). The effect of the α-derivatives of cis-monounsaturated fatty acids (250 µM, 6 h) on the activity and expression of the COX-1 and COX-2 cyclooxygenases was investigated in the same system. These fatty acids significantly inhibited the activity of COX-1 (FIG. 19A) and the expression of COX-2 (FIG. 19B). By contrast, compounds that did not have the structure of Formula I did not inhibit the expression of these proinflammatory cytokines (FIGS. 19A-19B).

These results indicate that α-derivatives of cis-monounsaturated fatty acids can be effective for the treatment of the autoimmune inflammatory disease known as rheumatoid arthritis by inhibiting the production of proinflammatory cytokines, the levels of which increase markedly in rheumatoid arthritis patients. The inhibition of COX-1 and COX-2 function by these fatty acids indicates that these compounds are useful in the treatment of pain and inflammation. These fatty acids can be considered to be a new generation of non-steroid anti-inflammatory drugs (NSAIDs). Thus, the inhibition of the activity of COX-1 and COX-2 functions indicates that these fatty acids can also be used for the treatment or prevention of cardiovascular diseases and reduce the risk of ischemic events such as heart attacks. Therefore, due to the important inhibition of the expression of proinflammatory cytokines by α-derivatives of cis-monounsaturated fatty acids, they can be used for the prevention and the treatment of inflammatory and derivative processes such as pain and rheumatoid arthritis, both at a systemic and a topical level, and through pharmaceutical, nutraceutical and topical/cosmetic preparations.

TABLE 4

Inhibition of the release of proinflammatory cytokines by OHHD.

| Cytokine | Control (pg/ml) | LPS (pg/ml) | LPS + OHHD (pg/ml) |
|---|---|---|---|
| IL-1b | 12 ± 2 | 132 ± 2 | 41 ± 5 |
| IL-6 | 24 ± 3 | 1072 ± 4 | 68 ± 8 |
| IL-8 | 345 ± 7 | 967 ± 8 | 529 ± 7 |
| IL-10 | 32 ± 1 | 315 ± 9 | 53 ± 3 |
| TNF-α | 15 ± 6 | 1504 ± 7 | 65 ± 9 |

$p < 0.001$.
Average ± standard error of 6 experiments performed in triplicate.

Example 8

Use of the Fatty Acids of the Invention for the Prevention and/or Treatment of Infectious Pathologies Acquired immunodeficiency syndrome (AIDS) is caused by infection with the human immunodeficiency picornavirus (HIV). This virus has a lipid covering and the integrity of the viral covering is essential for fusion with the human cellular membrane. The α-derivatives of cis-monounsaturated fatty acids modify the structure of model membranes, similar to those on the AIDS virus (FIG. 20), so that they can be used for the treatment of this disease.

The binding between HIV and the host cells is also mediated by the CD4 receptor. This eukaryote cell protein is located in specific regions of the cellular membrane known as "membrane rafts". The α-derivatives of cis-monounsaturated fatty acids break up the structure of the "lipid rafts", so they interfere in the virus-cellular interaction necessary to cause and amplify infection (FIG. 21A-C). Therefore, α-derivatives of cis-monounsaturated fatty acids can be used for the prevention and treatment of AIDS.

Malaria, like AIDS, is an infectious disease that in this case is caused by the protozoan known as *Plasmodium falciparum*. This organism has very rapid cell division, so it constantly needs to synthesise DNA. For synthesis of DNA, high levels of tetrahydrofolate are required, which acts as a co-enzyme for some enzymes that produce nucleotides for synthesising DNA. The enzyme that makes tetrahydrofolate is Dihydrofolate Reductase (DHFR). Therefore, inhibitors of DHFR such as methotrexate are currently being used to treat malaria (Nduati et al. 2008). The α-derivatives of cis-monounsaturated fatty acids induce a very marked reduction in this enzyme, which results in a significant fall in DHFR levels (FIG. 22), so they may have an important activity against malaria development. Compared to pharmaceuticals such as methotrexate, α-derivatives of cis-monounsaturated fatty acids have two advantages. Firstly, their toxicity is lower. Secondly, the reduction in the expression of the enzyme is a much more effective mechanism than its inhibition (which results in high levels of enzyme that can be activated at the end of the treatment). Therefore, α-derivatives of cis-monounsaturated fatty acids can be effective drugs for malaria treatment.

Also, agents that inhibit the production of tetrahydrofolate are effective antibacterial agents. This fact, together with the evidence presented in this example on the effectiveness of α-derivatives of cis-monounsaturated fatty acids against the development of infectious processes of diverse types indicates that these molecules can be effective agents for the prevention or treatment of infectious pathologies.

Example 9

Use of the Fatty Acids of the Invention and Various Salts for the Prevention and/or Treatment of Various Pathologies Certain atoms at defined locations on a molecule with pharmacological activity can change its absorption, distribution in the organism or its interaction with cellular macromolecules. This can imply changes in both a positive and a negative direction in the therapeutic effectiveness of an active ingredient. Table 5 shows the potential therapeutic effectiveness of various salts of α-derivatives of cis-monounsaturated fatty acids for the treatment of cancer, metabolopathies (hypercholesterolemia, hypertriglyceridemia), obesity and hypertension. In this sense, it was possible to demonstrate that the sodium salt of OHOD (Na—OHOD) is more effective than the free fatty acid for reversing various pathologies. The same was observed with Na-DEPOD compared to DEPOD. Therefore, in the formulation of medicines with α-derivatives of cis-monounsaturated fatty acids, it would be better to use the sodium derivatives of these substances.

TABLE 5

Therapeutic effects of various derivatives of α-derivatives of cis-monounsaturated fatty acids and their salts in various pathologies

| | $IC_{50}$ | | % control | | Body weight (g) (control = 311 g) | PA (control 214 mmHg) |
|---|---|---|---|---|---|---|
| | A549 | SF767 | CHO | TG | | |
| OHOD | 62 | 71 | 55 | 38 | 292 | 146 |
| Na-OHOD | 47 | 52 | 51 | 32 | 281 | 128 |
| OMe-OHOD | 94 | 107 | 71 | 64 | 299 | 155 |
| EE-OHOD | 79 | 68 | 62 | 47 | 295 | 161 |
| NH3-OHOD | 81 | 85 | 59 | 62 | 290 | 149 |
| ACOD | 153 | 179 | 59 | 53 | 301 | 157 |
| Na-ACOD | 124 | 132 | 49 | 35 | 298 | 166 |
| OMe-ACOD | 246 | 214 | 86 | 74 | 296 | 152 |
| EE-ACOD | 185 | 176 | 72 | 56 | 294 | 158 |
| MOOD | 61 | 73 | 65 | 64 | 279 | 142 |
| Na-MOOD | 77 | 91 | 63 | 68 | 272 | 131 |
| OMe-MOOD | 149 | 128 | 77 | 69 | 296 | 143 |
| EE-MOOD | 168 | 195 | 64 | 66 | 297 | 154 |
| DEPOD | 57 | 99 | 58 | 43 | 301 | 147 |
| Na-DEPOD | 32 | 104 | 45 | 37 | 298 | 159 |
| OMe-DEPOD | 66 | 43 | 63 | 45 | 293 | 175 |
| EE-DEPOD | 77 | 82 | 69 | 49 | 295 | 168 |

OHOD: α-Hidroxy-cis-Δ9-octadecenoic;
ACOD: α-Acetyl-cis-Δ9-octadecenoic;
MOOD: α-Methoxy-cis-Δ9-octadecenoic;
DEPOD: α-diethyl-phosphatidyl-cis-Δ9-octadecenoic.

The atom or molecule that replaces the R in Formula I is sodium (with prefix "Na"), methyl ester (OMe), ethyl ester (EE), ammonium (NH3) or hydrogen (no prefix). The parameter measured for determining the anti-tumour potency was the $IC_{50}$ (concentration that reduces the number of cells to half) in A549 and SF767 human tumour cells. The values are expressed in micromolar concentration (μM). The second column shows the levels of cholesterol (CHO) and triglycerides (TG) in percent compared to untreated controls (100%). Rats received a daily dose of 600 mg/kg of substances indicated in the table (for other details on the treatment, see the text). The third column shows the body weight (g) of rats receiving a cafeteria diet for 2 weeks. Control rats, which weighed 311 g at the end of the treatment (average of 6 animals), received vehicle (water), whereas treated animals received 300 mg/kg daily of the substances indicated in the table.
PA: arterial pressure (mmHg).
The arterial pressure was measured in hypertensive rats after an 8-day treatment with each of the compounds indicated (400 mg/kg). As indicated in the table header, the average PA of untreated rats was 214 mmHg. In all the experimental series with animals shown in this table, the treatments were always oral.

REFERENCES

1. Alemany R, Perona J S, Sánchez-Domínguez J M, Montero E, Cañizares J, Brezan R, Escribá P V and Ruiz-Gutiérrez V (2007). G protein-coupled receptor systems and their lipid environment in health disorders during aging. *BBA Biomembr.* 1768:964-975.
2. Barnes P J, Karin M (1997). Nuclear factor-kappaB: a pivotal transcription factor in chronic inflammatory diseases. *N Engl J Med* 336:1066-71.
3. Buda C, Dey I, Balogh N, Horvath L I, Maderspach K, Juhasz M, Yeo Y K, Farkas T (1994). Structural order of membranes and composition of phospholipids in fish brain cells during thermal acclimatization. *Proc. Natl. Acad. Sci USA* 91:8234-8238.
4. Curto E V, Kwong C, Hersmerdorfer H, Glatt H, Santis C, Virador V, Hearing V J, Jr., Dooley T P (1999). *Biochem Pharmacol* 57:663-672.
5. Escriba P V, Sastre M, Garcia-Sevilla J A. (1995). Disruption of cellular signaling pathways by daunomycin through destabilization of nonlamellar membrane structures. Proc Natl Acad Sci USA. 92:7595-7599.
6. Escriba P V, Ozaita A, Ribas C, Miralles A, Fodor E, Farkas T, García-Sevilla J A (1997). Role of lipid polymorphism in G protein-membrane interactions: nonlamellar-prone phospholipids and peripheral protein binding to membranes. Proc Natl Acad Sci USA. 94:11375-11380.
7. Escribá PV (2006). Membrane-lipid therapy: a new approach in molecular medicine. *Trends Mol. Med.* 12:34-43.
8. Escribá PV, González-Ros J M, Goñi F M, Kinnunen P K J, Vigh L, Sánchez-Magraner L, Fernández A M, Busquets X, Horváth I, Barceló-Coblijn G (2008). Membranes: A meeting point for lipids, proteins and therapies. *J Cell. Mol. Med.* 12:829-875.
9. Martínez J O, Casas J F, Alemany R, Prades J, Nagy T, Baamonde C, Kasprzyk P, Terés S, Saus C, Escribá P V. (2005). Membrane structure modulation, protein kinase C alpha activation, and anticancer activity of minerval. *Mol Pharmacol* 67:531-40.
10. Nduati et al. (2008). Effect of folate derivatives on the activity of antifolate drugs used against malaria and cancer. *Parasitol Res* 102: 1227-1234.
11. Patil C S, Singh V P, Kulkarni S K (2006). Modulatory effect of Sildefanil in diabetes and electroconvulsive shock-induced cognitive dysfunction in rats. *Pharmacological Reports* 58: 373-380.
12. Raid P C, Urano Y, Kodama T, Hamakubo T (2007). Alzheimer's disease: cholesterol, membrane rafts, isoprenoids and statins. *J Cell Mol Med* 11:383-392.
13. Stender S, Dyerberg J (2004). Influence of trans fatty acids on health. *Ann. Nutr. Metab.* 48:61-66.
14. Wise L E, Iredale P A, Stokes R J, Litchman A H (2007). Combination of Rimonabant and Donepezil prolongs spatial memory duration. Neuropsychopharmacology 32: 1805-1812.
15. Yang, Q, Alemany, R, Casas, J, Kitajka, K, Lanier, S M, Escribá P V (2005). Influence of the membrane lipid structure on signal processing via G protein-coupled receptors. *Mol Pharmacol* 68:210-7.

The invention claimed is:

1. A method for the therapeutic treatment of an inflammatory process and/or pain in humans and mammals, wherein said inflammatory process results in pain, comprising the administration to said human or mammal of a therapeutically effective amount of at least one pharmaceutically acceptable compound of Formula I or a salt thereof, independently or in combination with at least one other compound,

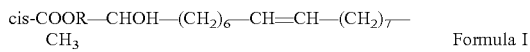

Formula I where (R) is one of H, sodium, or ammonium.

2. The method according to claim 1, for the therapeutic treatment of pain, wherein said pain is caused by an inflammatory process.
3. The method according to claim 1, for the therapeutic treatment of pain, wherein said pain is caused by damage to the central nervous system.
4. The method according to claim 1, wherein the at least one other compound is albumin.
5. The method according to claim 1, wherein the compound of Formula I is α-hydroxy-cis-Δ9-octadecenoic acid (OHOD).

6. The method according to claim 1, wherein the compound of Formula I is selected from the group consisting of α-hydroxy-cis-Δ9-octadecenoic acid (OHOD), the sodium salt of α-hydroxy-cis-Δ9-octadecenoic acid (Na—OHOD), and the ammonium salt of α-hydroxy-cis-Δ9-octadecenoic acid.

7. The method according to claim 1, comprising the administration to said human or mammal of a therapeutically effective amount of cis-COOH—CHOH—$(CH_2)_6$—CH=CH—$(CH_2)_7$—$CH_3$ or cis-COONa—CHOH—$(CH_2)_6$—CH=CH—$(CH_2)_7$—$CH_3$, independently or in combination with albumin.

8. The method according to claim 1, for the therapeutic treatment of pain, wherein said pain is neuropathic pain.

9. The method according to claim 4, for the therapeutic treatment of pain, wherein said pain is acute pain.

10. The method according to claim 4, for the therapeutic treatment of pain, wherein said pain is chronic pain.

11. The method according to claim 1, for the therapeutic treatment of pain, wherein said pain is caused by changes in nociperception.

12. The method according to claim 1, for the therapeutic treatment of pain, wherein said pain is caused by processes that require analgesia.

13. The method according to claim 8, for the therapeutic treatment of neuropathic pain, wherein the administration to said human or mammal of a therapeutically effective amount of at least one pharmaceutically acceptable compound of Formula I is oral administration and wherein the compound of Formula I is selected from the group consisting of α-hydroxy-cis-Δ9-octadecenoic acid (OHOD), the sodium salt of α-hydroxy-cis-Δ9-octadecenoic acid (Na—OHOD), and the ammonium salt of α-hydroxy-cis-Δ9-octadecenoic acid.

14. The method according to claim 13, wherein the compound of Formula I is α-hydroxy-cis-Δ9-octadecenoic acid (OHOD).

15. The method according to claim 13, wherein the compound of Formula I is the sodium salt of α-hydroxy-cis-Δ9-octadecenoic acid (Na—OHOD).

* * * * *